(12) United States Patent
Piskun et al.

(10) Patent No.: US 8,888,695 B2
(45) Date of Patent: Nov. 18, 2014

(54) LAPAROSCOPIC PORT ASSEMBLY

(75) Inventors: Gregory Piskun, Brooklyn, NY (US);
Christopher Battles, Seymour, CT (US); Frank Rende, Westport, CT (US); Michael Abrams, New Haven, CT (US); Oleg Shikman, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 902 days.

(21) Appl. No.: 12/079,599

(22) Filed: Mar. 27, 2008

(65) Prior Publication Data

US 2008/0255519 A1    Oct. 16, 2008

Related U.S. Application Data

(60) Provisional application No. 60/920,935, filed on Mar. 30, 2007.

(51) Int. Cl.
*A61B 1/32* (2006.01)
*A61B 17/34* (2006.01)
*A61B 1/313* (2006.01)

(52) U.S. Cl.
CPC ............... *A61B 1/32* (2013.01); *A61B 17/3423* (2013.01); *A61B 2017/3445* (2013.01); *A61B 2017/3447* (2013.01); *A61B 17/3439* (2013.01); *A61B 1/3132* (2013.01); *A61B 2017/349* (2013.01); *A61B 2017/3427* (2013.01); *A61B 2017/3466* (2013.01); *A61B 17/3421* (2013.01)
USPC .............................. 600/214; 600/225; 600/233

(58) Field of Classification Search
USPC ......... 600/114, 165, 211, 214, 566, 201–208, 600/225, 229, 233; 604/158, 604/164.01–164.04, 164.09, 164.1, 164.11, 604/170.02, 170.03, 264, 528, 533–536, 604/284, 288.04, 514, 539; 606/108, 304
See application file for complete search history.

(56) References Cited

U.S. PATENT DOCUMENTS

| | | | | |
|---|---|---|---|---|
| 1,827,497 A | * | 10/1931 | Varney | 606/198 |
| 2,669,991 A | | 2/1954 | Curutchet | |
| 4,608,965 A | * | 9/1986 | Anspach et al. | 600/101 |
| 4,644,951 A | | 2/1987 | Bays | |
| 4,863,430 A | | 9/1989 | Klyce et al. | |
| 5,183,471 A | | 2/1993 | Wilk | |
| 5,241,968 A | | 9/1993 | Slater | |
| 5,242,409 A | | 9/1993 | Buelina | |
| 5,269,772 A | | 12/1993 | Wilk | |

(Continued)

FOREIGN PATENT DOCUMENTS

| | | |
|---|---|---|
| DE | 19828099 A1 * | 12/1999 |
| JP | 05-293112 | 11/1993 |

(Continued)

OTHER PUBLICATIONS

International Search Report of PCT/US08/03991 dated Jul. 30, 2008. (1 Page).

(Continued)

*Primary Examiner* — Pedro Philogene
*Assistant Examiner* — Lynnsy Summitt

(57) ABSTRACT

Various embodiments of a laparoscopic trocar assembly are disclosed. The port assemblies include inserted parts that protect the patient's tissues at the point of deployment. The port assemblies include seals for maintaining pneumoperitoneum both when instrument are being used and when instruments are not inserted.

3 Claims, 23 Drawing Sheets

(56) References Cited

U.S. PATENT DOCUMENTS

| | | | |
|---|---|---|---|
| 5,312,391 A | 5/1994 | Wilk | |
| 5,330,486 A | 7/1994 | Wilk | |
| 5,366,478 A | 11/1994 | Brinkerhoff et al. | |
| 5,391,156 A | 2/1995 | Hildwein et al. | |
| 5,395,327 A | 3/1995 | Lundquist et al. | |
| 5,395,367 A | 3/1995 | Wilk | |
| 5,480,410 A | 1/1996 | Cuschieri et al. | |
| 5,509,893 A * | 4/1996 | Pracas | 600/224 |
| 5,549,563 A | 8/1996 | Kronner | |
| 5,549,637 A | 8/1996 | Crainich | |
| 5,571,115 A | 11/1996 | Nicholas | |
| 5,571,137 A | 11/1996 | Marlow et al. | |
| 5,575,799 A | 11/1996 | Bolanos et al. | |
| 5,578,048 A | 11/1996 | Pasqualucci et al. | |
| 5,634,937 A | 6/1997 | Mollenauer et al. | |
| 5,651,771 A | 7/1997 | Tangherlini et al. | |
| 5,672,168 A | 9/1997 | De La Torre et al. | |
| 5,725,536 A | 3/1998 | Oberlin et al. | |
| 5,782,859 A | 7/1998 | Nicholas et al. | |
| 5,836,871 A | 11/1998 | Wallace et al. | |
| 5,860,995 A | 1/1999 | Berkelaar | |
| 5,906,577 A | 5/1999 | Beane et al. | |
| 5,931,832 A | 8/1999 | Jensen | |
| 5,957,913 A | 9/1999 | de la Torre et al. | |
| 5,964,781 A | 10/1999 | Mollenauer et al. | |
| 6,086,603 A | 7/2000 | Termin et al. | |
| 6,099,506 A | 8/2000 | Macoviak et al. | |
| 6,142,931 A | 11/2000 | Kaji | |
| 6,142,936 A | 11/2000 | Beane et al. | |
| 6,217,590 B1 | 4/2001 | Levinson | |
| 6,264,604 B1 | 7/2001 | Kieturakis et al. | |
| 6,440,063 B1 | 8/2002 | Beane et al. | |
| 6,447,489 B1 | 9/2002 | Peterson | |
| 6,458,077 B1 | 10/2002 | Boebel et al. | |
| 6,468,292 B1 | 10/2002 | Mollenauer et al. | |
| 6,551,270 B1 | 4/2003 | Bimbo et al. | |
| 6,676,639 B1 | 1/2004 | Ternström | |
| 6,706,050 B1 | 3/2004 | Giannadakis | |
| 6,878,110 B2 | 4/2005 | Yang et al. | |
| 6,887,193 B2 | 5/2005 | Bacher et al. | |
| 6,890,295 B2 | 5/2005 | Michels et al. | |
| 6,916,331 B2 | 7/2005 | Mollenauer et al. | |
| 7,008,377 B2 | 3/2006 | Beane et al. | |
| 7,195,592 B2 * | 3/2007 | Ravikumar et al. | 600/219 |
| 7,223,257 B2 | 5/2007 | Shubayev et al. | |
| 7,300,399 B2 | 11/2007 | Bonadio et al. | |
| 7,753,901 B2 | 7/2010 | Piskun et al. | |
| 2002/0183594 A1 | 12/2002 | Beane et al. | |
| 2003/0014076 A1 | 1/2003 | Mollenauer et al. | |
| 2003/0036748 A1 | 2/2003 | Cooper et al. | |
| 2005/0215863 A1* | 9/2005 | Ravikumar et al. | 600/204 |
| 2005/0273133 A1* | 12/2005 | Shluzas et al. | 606/198 |
| 2006/0149306 A1 | 7/2006 | Hart et al. | |
| 2006/0241651 A1 | 10/2006 | Wilk | |
| 2006/0247498 A1 | 11/2006 | Bonadio et al. | |
| 2007/0151566 A1 | 7/2007 | Kahle et al. | |
| 2007/0203398 A1 | 8/2007 | Bonadio et al. | |
| 2007/0208312 A1 | 9/2007 | Norton et al. | |
| 2007/0270654 A1* | 11/2007 | Pignato et al. | 600/208 |
| 2008/0103366 A1* | 5/2008 | Banchieri et al. | 600/208 |
| 2009/0012477 A1 | 1/2009 | Norton et al. | |

FOREIGN PATENT DOCUMENTS

| | | |
|---|---|---|
| JP | 2004-041580 | 2/2004 |
| WO | WO 96/33667 A1 | 10/1996 |
| WO | WO 97/42889 | 11/1997 |
| WO | WO 2006/019723 A2 | 2/2006 |

OTHER PUBLICATIONS

Translation of Japanese Office Action for Application No. 2010-500992 (6 pages).

Extended European Search Report corresponding to EP 08 74 2301.8, completed Jan. 21, 2014 and mailed Jan. 28, 2014; (11 Pages).

* cited by examiner

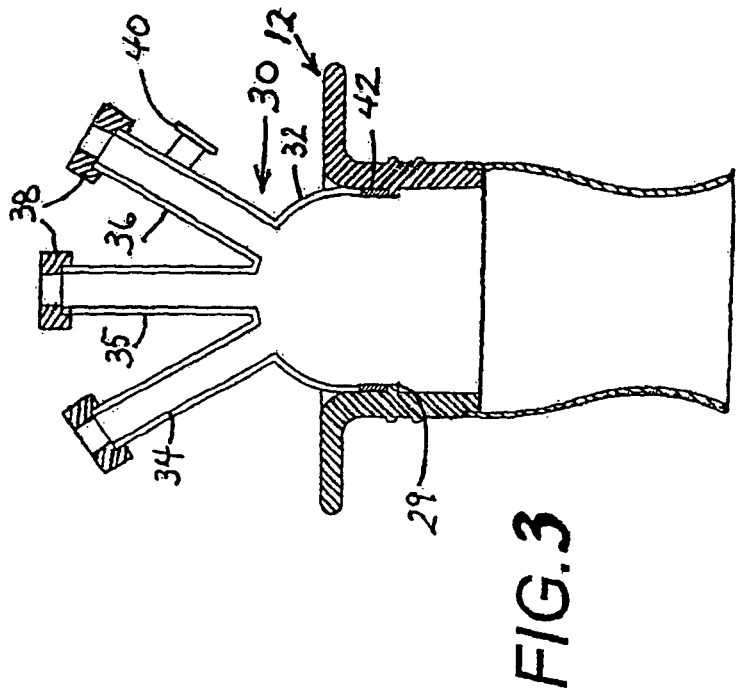
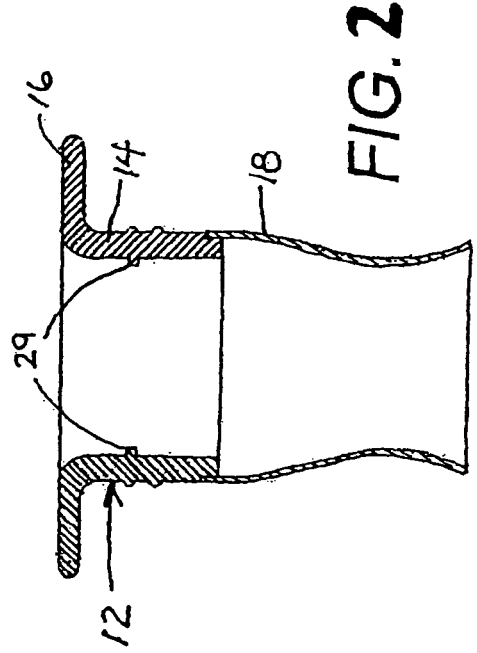
FIG. 2
FIG. 3

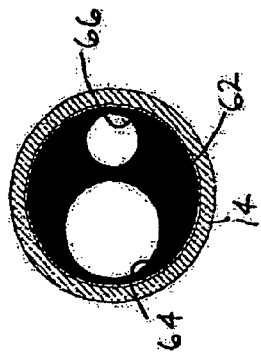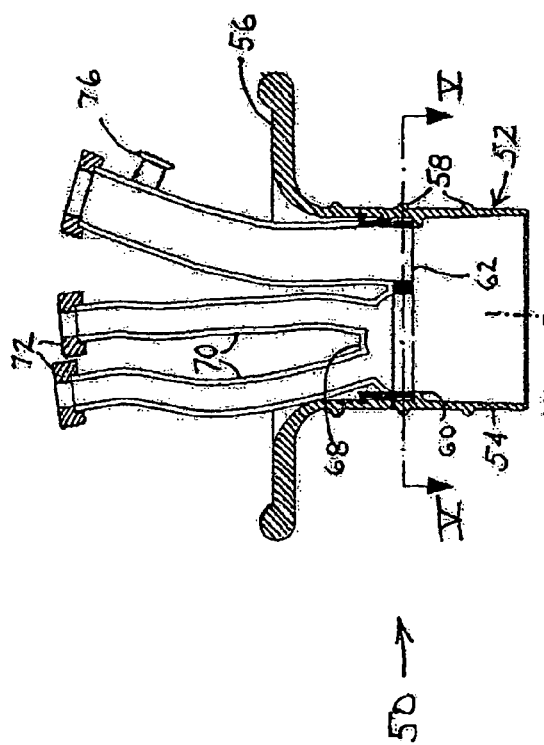

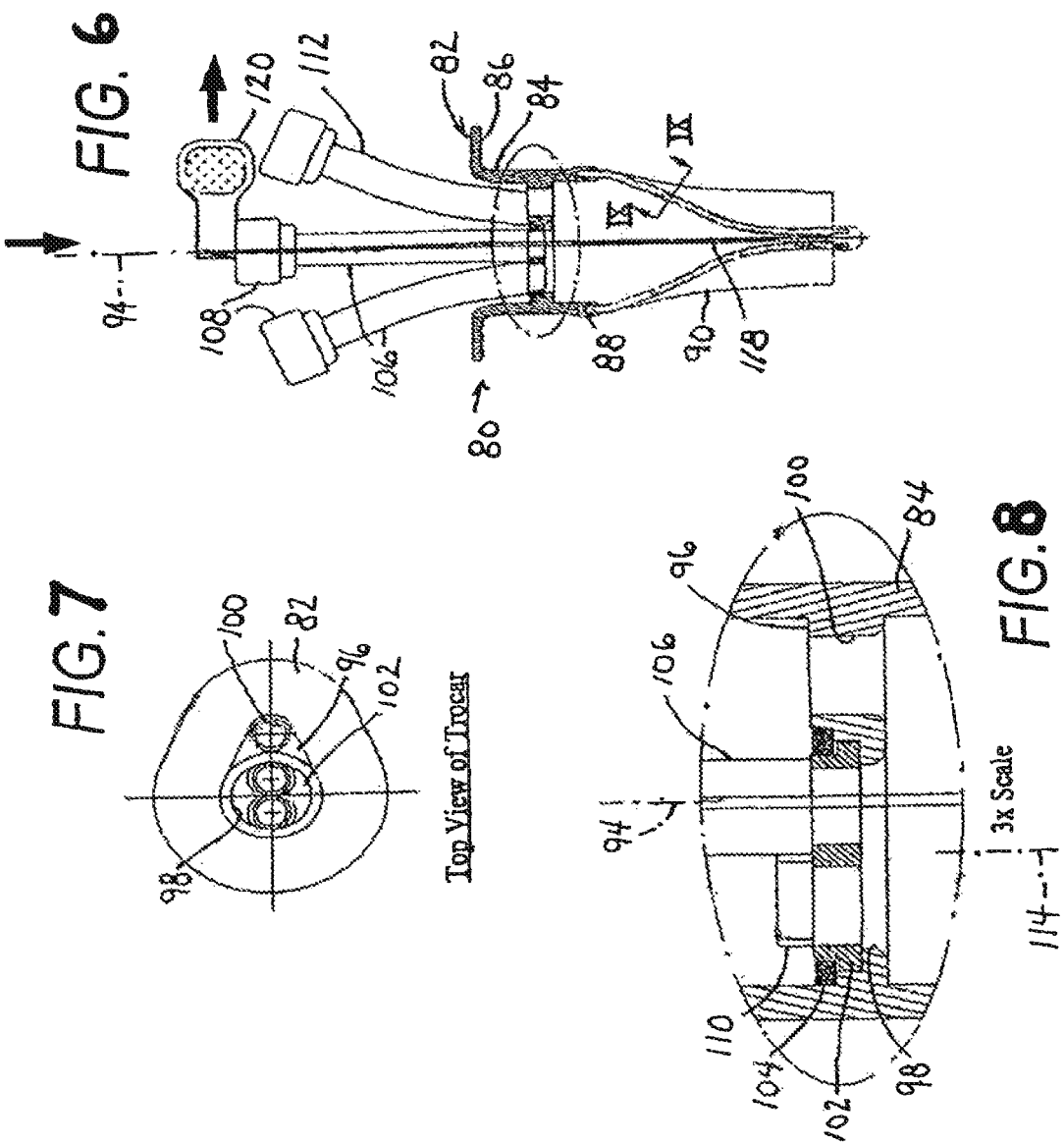

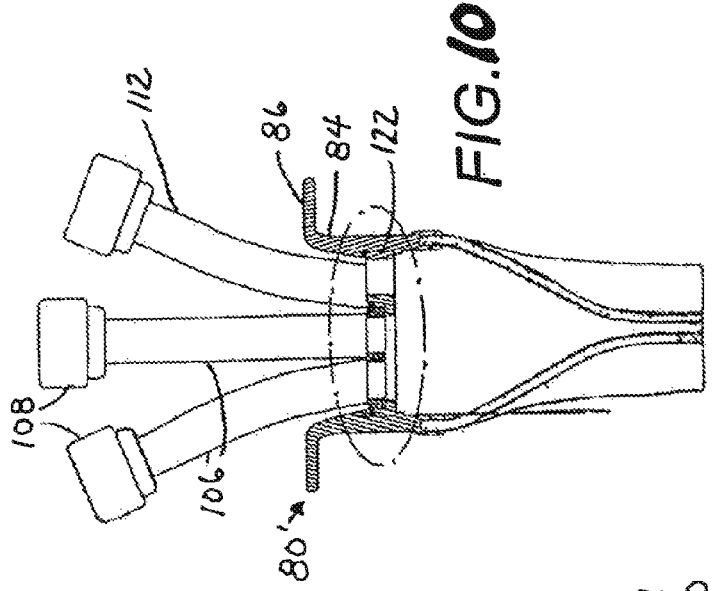
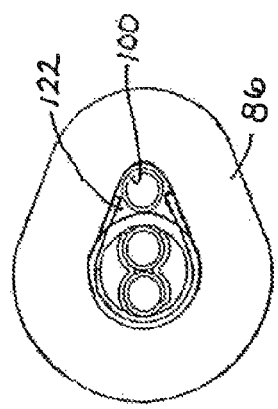
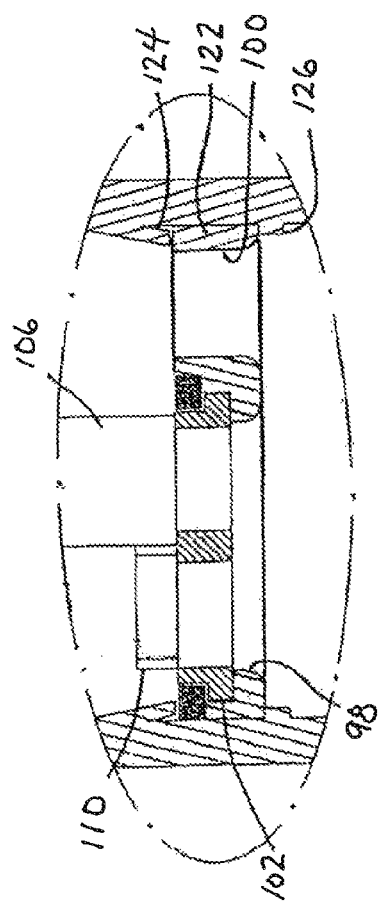

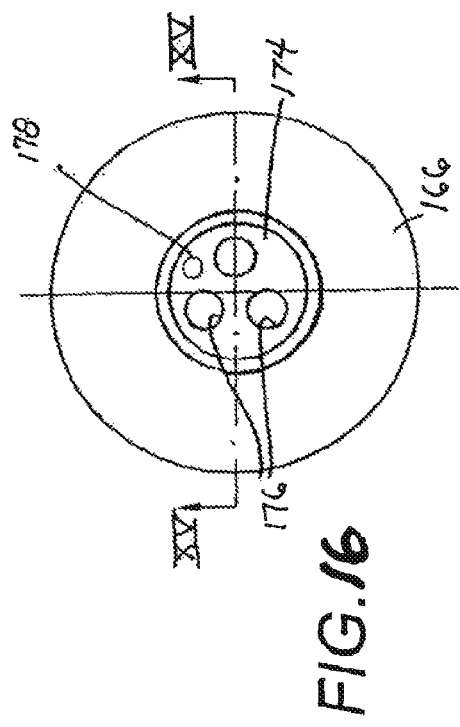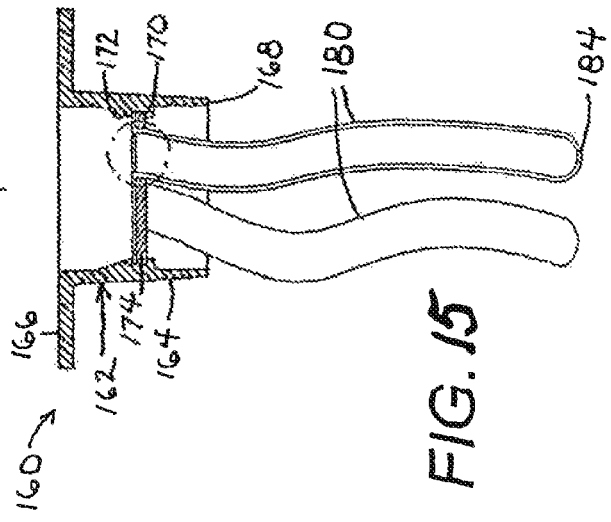

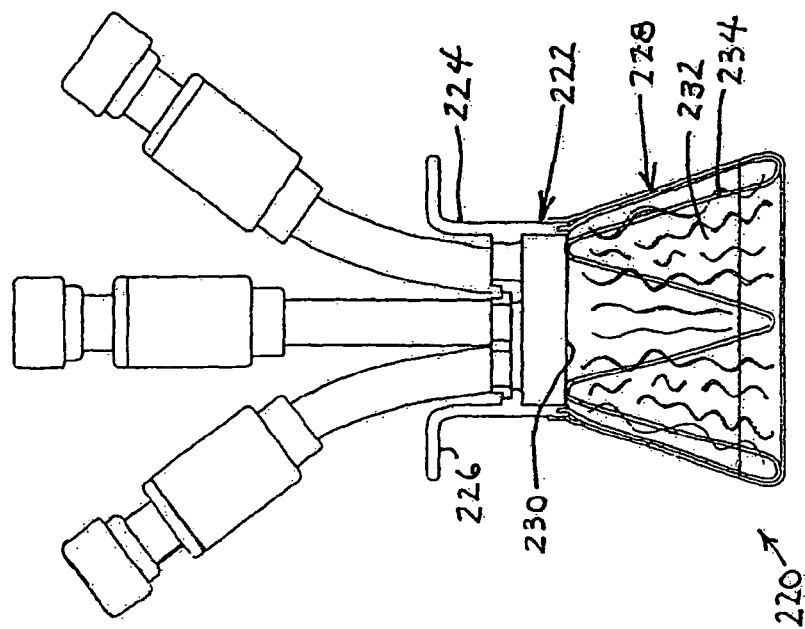
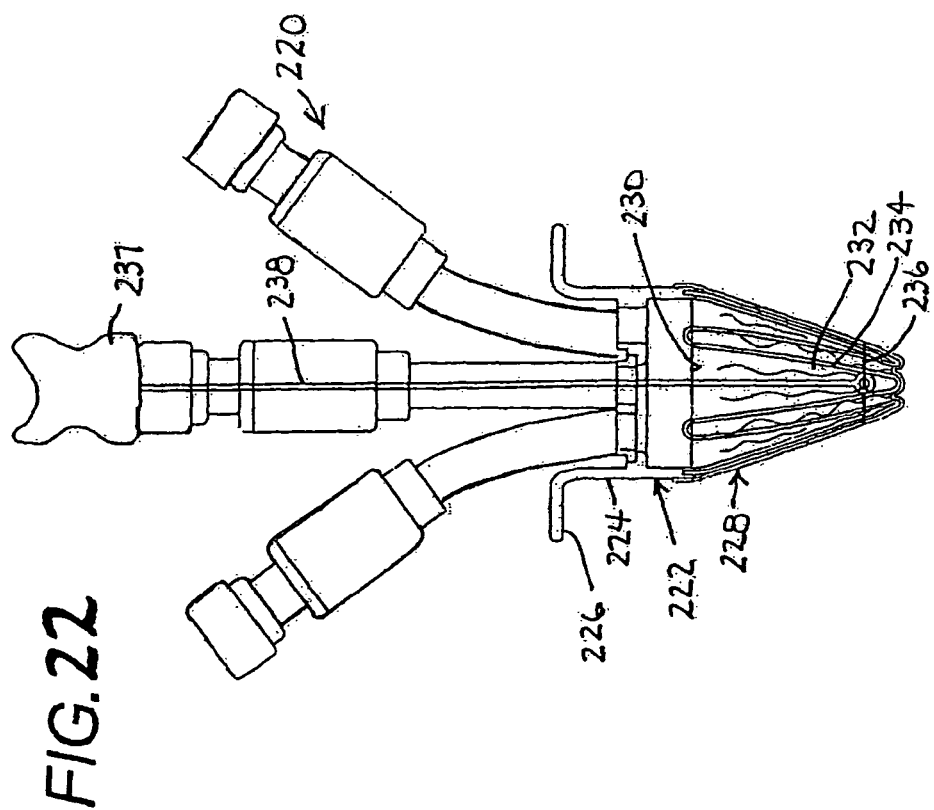

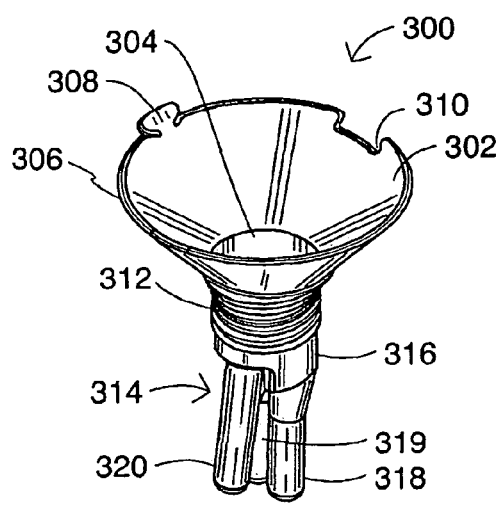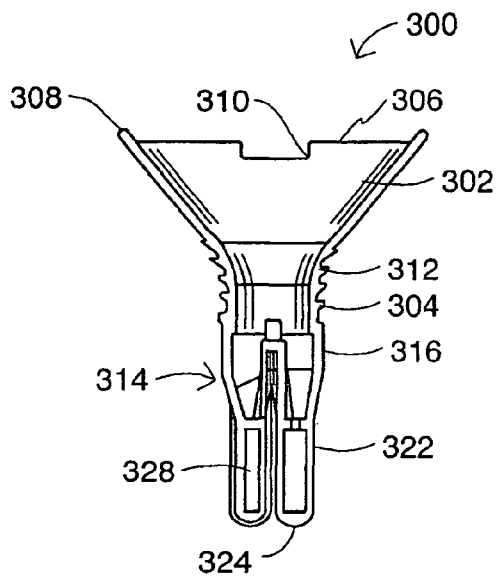
FIG. 37
FIG. 38
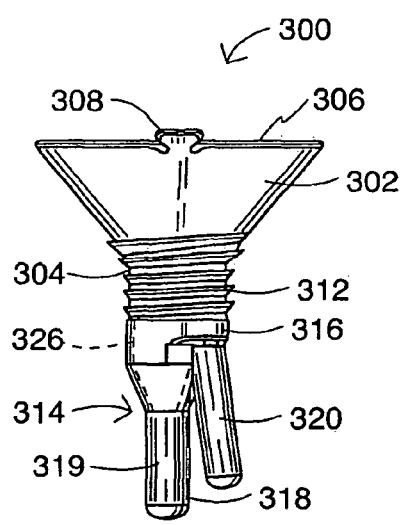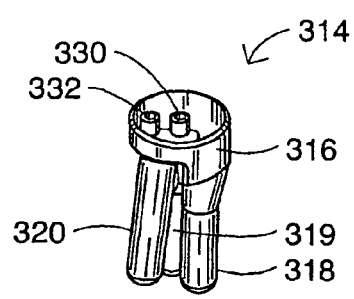
FIG. 39
FIG. 40

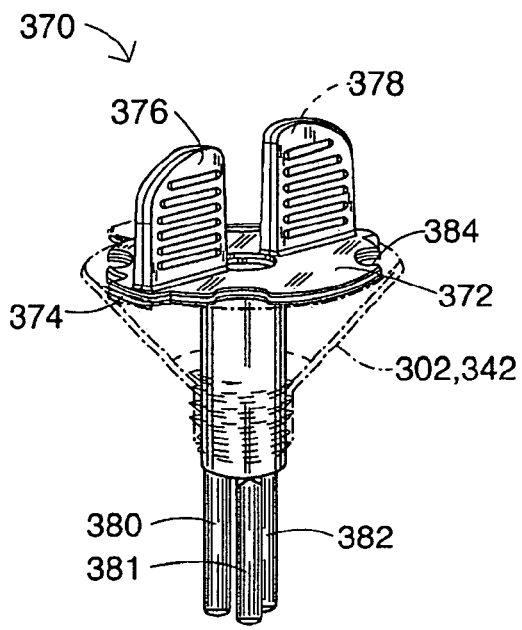
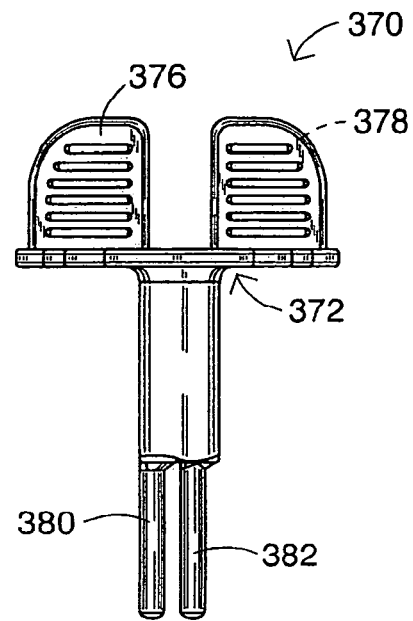
FIG. 45          FIG. 46
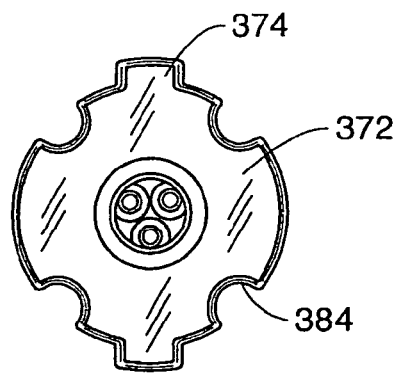
FIG. 47

LAPAROSCOPIC PORT ASSEMBLY

CROSS-REFERENCE TO RELATED APPLICATION

This application claims the benefit of U.S. Provisional Patent Application No. 60/920,935 filed Mar. 30, 2007.

FIELD OF THE INVENTION

The present invention relates to surgical port assemblies. The port assemblies of the present invention are particularly useful in minimally invasive surgical procedures such as laparoscopic operations entirely through the umbilicus.

BACKGROUND OF THE INVENTION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with C02 gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through (one of) the trocar sleeve(s). Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. However, instruments used for mini-laparoscopic procedures are generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedure. In addition, smaller, 2-3 mm, incisions may still cause undesirable cosmetic outcomes and wound complications (bleeding, infection, pain, keloid formation, etc.).

Since the benefits of smaller and fewer body cavity incisions are proven, it would be attractive to perform an operation utilizing only a single incision in the navel. An umbilicus is the thinnest and least vascularized, and a well-hidden, area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems, which allow laparoscopic procedures to be performed entirely through the umbilicus while at the same time reducing or eliminating the "chopstick effect." A laparoscopic procedure performed entirely through the umbilicus, using the laparoscopic instruments and trocar system according to an embodiment of the present invention, allows one to accomplish the necessary diagnostic and therapeutic tasks while further minimizing abdominal wall trauma and improving cosmesis.

OBJECTS OF THE INVENTION

The present invention provides cannula or port assemblies for the performance of surgical procedures, particularly including laparoscopic procedures, for instance, entirely through the umbilicus.

An object of the present invention is to provide an improved port assembly for facilitating access to internal organs of a patient during laparoscopic procedures.

Another object of the present invention is to provide such a port assembly that provides enlarged workspace for the hands of the surgeon(s) when plural laparoscopic instruments are placed through the umbilicus.

These and other objects of the invention will be apparent from the drawings and descriptions herein. Although each object of the invention is believed to be attained by at least one embodiment of the invention, there is not necessarily any single embodiment that achieves all of the objects of the invention.

SUMMARY OF THE INVENTION

The present invention facilitates the performance of laparoscopic surgical procedures wherein several laparoscopic instruments are inserted into a patient through respective cannulas all extending through the same opening in the patient, for instance, through the umbilicus. The advantages of such an operation include minimizing trauma to the patient and accelerating the patient recovery.

A first embodiment of a surgical port assembly in accordance with the present invention comprises a body attachable to a patient at an incision in a skin surface of the patient to facilitate deployment of instruments in the patient via the incision. The body has a main axis oriented substantially transversely to the patient's skin surface upon disposition of the body in the incision. The port assembly further comprises a main first plate, a second plate, at least one first tubular member and a second tubular member. The first plate has a first opening and a second opening and is mounted to the body substantially transversely to the axis. The second plate is rotatably disposed in the first opening for turning about an auxiliary axis preferably substantially parallel to the main axis. The first tubular member is attached to the second plate and extends in at least one direction away from the second plate. The second tubular member is attached to the first plate at the second opening and extends in at least one direction away from the first plate.

The body of the port assembly has an outer side facing away from the patient and an inner side facing inwardly of or towards the patient's skin surface during a surgical procedure. Pursuant to one alternative design of the port assembly, the first tubular member extends only upwardly or outwardly away from the second plate, on the outer side of the body. Preferably, the first tubular member is one of a plurality of first tubular members all attached to the second plate and extending only upwardly or outwardly away from the second plate, on the outer side of the body. According to a specific feature of this design, at least one of the first tubular members is flexible at least at a point of attachment to the second plate, enabling a pivoting (about a transverse axis) and/or a swiveling (about a longitudinal axis) at the second plate of a surgical instrument inserted through the at least one of the first tubular members. The first tubular members are each provided with at least one seal for maintaining pneumoperitoneum when a surgical instrument shaft longitudinally traverses such first tubular member and at least one seal for maintaining pneumoperitoneum in the absence of a surgical instrument shaft longitudinally traversing such first tubular member.

Pursuant to another alternative design of the port assembly, the first tubular member extends only downwardly or inwardly away from the second plate, on the inner side of the body. Preferably in this design, the first tubular member is one of a plurality of first tubular members all attached to the second plate and extending only downwardly or inwardly away from the second plate, on the inner side of the body. According to a specific feature of this alternative design, at least one of the first tubular members is flexible at least at a point of attachment to the second plate, enabling a pivoting (about a transverse axis) and/or a swiveling (about a longitudinal axis) at the second plate of a surgical instrument inserted through the at least one of the first tubular members. Again, the first tubular members are each provided with at least one seal for maintaining pneumoperitoneum when a surgical instrument shaft longitudinally traverses such first tubular member and at least one seal for maintaining pneumoperitoneum in the absence of a surgical instrument shaft longitudinally traversing such first tubular member.

Pursuant to additional features of the present invention, the second plate is dome-shaped and the second plate is removably attached to the first plate.

A second embodiment of a surgical port assembly in accordance with the present invention comprises a body attachable to a patient at an incision in a skin surface of the patient to facilitate deployment of instruments in the patient via the incision, the body having an outer side facing away from the patient and an inner side facing inwardly of or towards the patient's skin surface during a surgical procedure. At least one tubular member depends downwardly or inwardly from the body so that the tubular member is disposed only on the inner side of the body.

The downwardly depending tubular member is preferably one of a plurality of tubular members all depending downwardly or inwardly from the body so that the tubular members are disposed only on the inner side of the body. Each of the tubular members is preferably provided with at least one seal for maintaining pneumoperitoneum when a surgical instrument shaft longitudinally traverses such tubular member and additionally provided with at least one seal for maintaining pneumoperitoneum in the absence of a surgical instrument shaft longitudinally traversing such tubular member.

The downwardly depending tubular members may be made fully or partially of elastomeric material. Preferably, the tubular members are tiltable at least at an upper end In accordance with a further feature of the present invention, the downwardly depending tubular members are each provided along an inner surface with a rigid sleeve so arranged that the tubular members are each pivotable about a point of attachment to the body.

The body of the port assembly may have a funnel shape. In that case, the tubular members are attached to the funnel shape at an apical end thereof. The funnel shape may be a truncated cone that may have a circular, elliptical, oval or other cross-section.

In this second embodiment of the present invention, the outer side of the port assembly's body is free of upwardly or outwardly extending tubular cannula members and comprises a rim portion and a plate surrounded by the rim portion, the tubular members being connected to the plate and extending only on an inner side of the plate. The rim portion may sit on the skin surface of the patient and be attached thereto via adhesive. Alternatively, the rim portion may insert at least partially into the incision in the skin surface. In either case, the rim portion may have a circular or annular configuration.

The one or more downwardly depending tubular members may be detachably attached to the port assembly's body. In that case, the tubular member or members are fixed to a coupling member that in turn is detachably attached to the body at an aperture in the body. The port assembly may further comprise a plug to temporarily seal the aperture upon removal of the coupling member from the aperture.

Pursuant to another feature of the invention, the singular downwardly depending tubular member or one of the multiple downwardly depending tubular members carries a camera at a free end. The camera-carrying tubular member may be provided with directional cables that are actuatable from the outer or upper side of the port assembly for changing an orientation of the free end of the respective tubular member and the camera.

A third embodiment of a surgical port assembly comprise, in accordance with the present invention, a body attachable to a patient at an incision in a skin surface of the patient to facilitate deployment of instruments in the patient via the incision, the body having an outer side facing away from the patient and an inner side facing inwardly of or towards the patient's skin surface during a surgical procedure. A funnel-shaped extension is provided on the outer side of the body. The body together with the funnel-shaped extension may be made of a rigid metallic or polymeric material or a tough elastomeric material with some resilience and flexibility.

An obturator for deployment of a surgical port assembly (such as the second embodiment described above) through a skin surface comprises a body member, locking formations on the body member releasably engageable with cooperating locking formations on the port assembly, at least two finger contact surfaces on the body member, the finger contact surfaces facing in substantially opposed directions, for enabling manual application of a torque to the body member, and at least one elongate rigid member extending away from the body member on a side thereof opposite the finger contact surfaces, for penetrating through a skin surface.

The rigid member may be one of a plurality of parallel elongate rigid members extending away from the body member on a side thereof opposite the finger contact surfaces, for penetrating through a skin surface. The multiple rigid members of the obturator insert into respective downwardly depending tubular members of the second port assembly embodiment described above. The rigid members of the obturator thus serve to stiffen and hold the tubular members when the port assembly is being deployed at the onset of a minimally invasive surgical procedure, for example, a laparoscopic or thoracoscopic operation.

Accordingly, it is contemplated that the obturator is a component of a surgical access assembly or kit that further comprises a surgical port assembly including (a) a port assembly body attachable to a patient at an incision in a skin surface of the patient to facilitate deployment of instruments in the patient via the incision, the body having an outer side facing away from the patient and an inner side facing inwardly of or towards the patient's skin surface during a surgical procedure, and (b) a plurality of elastomeric tubular members all depending downwardly or inwardly from the port assembly body so that the tubular members are disposed only on the inner side of the body, the tubular members receiving respective ones of the elongate rigid members.

The locking formations may include projections on the body member or the obturator and recesses on the port assembly. The body member may take the form of a disk, which is provided with at least one cutout for enabling passage of an insufflation tube.

A surgical port assembly in accordance with one embodiment of the present invention comprises a body member and a skirt member. The body member is attachable to a patient at an incision in a skin surface of the patient to facilitate deployment of instruments in the patient via the incision, the body having an outer side facing away from the patient and an inner side facing inwardly of or towards the patient's skin surface during a surgical procedure. The skirt member is at least partially flexible and is attached to the body on the inner side thereof.

This embodiment of a surgical port assembly in accordance with the present invention may further comprise a trocar member insertable through the body and traversing the body during a deployment procedure. The skirt member has a collapsed or folded-in insertion configuration, wherein the skirt member is releasably attached to the trocar member during the deployment procedure. A portion of the skirt member may be removably inserted into a slot in the trocar member, to hold the skirt member in the folded-in configuration.

The skirt member may have a tapered expanded configuration wherein a free end of the skirt member, opposite the body member, has a larger transverse dimension that an end of the skirt attached to the body member.

The skirt member may include a flexible web member and a resilient support wire connected to the web member for expanding the web member from a folded-in insertion configuration to an expanded use configuration.

The skirt member may include flexible strip areas interleaved or alternating with more rigid areas.

Pursuant to additional specific features of the present invention, the body member may include a cylindrical portion, a dome on an upper or proximal side of the cylindrical portion, and a circumferential or annular disk-shaped flange, the dome being formed with a plurality of openings for passage of laparoscopic or thoracoscopic instrument shafts and a laparoscope or endoscope. The skirt member includes a cylindrical section engaging the cylindrical portion of the body and further includes a tapered or conical portion.

A related surgical port element in accordance with the present invention comprises a skirt made at least partially of flexible material and means for attaching the skirt to a cannula or instrument holder in turn removably attachable to a patient at an opening in a skin surface. The skirt has a folded-in insertion configuration and an expanded use configuration.

A surgical port component comprises, in accordance with the present invention, a body including a cylindrical portion formed by a plurality of cylindrical sections or flaps. The body further includes a ring-shaped base member, the cylindrical sections or flaps being swingably coupled to the base member. The cylindrical sections or flaps are made of at least a substantially rigid material, and the base member is provided with at least one upwardly or proximally extending arcuate flange section receivable into a distal or lower end of a cylindrical body of a flexible-cannula port member. An at least partially flexible skirt may be coupled to the body of the port component, for instance, by a cylindrical proximal sleeve section of the skirt fitting over the cylindrical sections or flaps.

Another surgical port assembly in accordance with the present invention comprises a body member and a flexible scope arm. The body member is attachable to a patient at an incision in a skin surface of the patient to facilitate deployment of instruments in the patient via the incision, the body member having an outer side facing away from the patient and an inner side facing inwardly of or towards the patient's skin surface during a surgical procedure. The flexible scope arm is connected to the body member and extends from an underside of the body member. The scope arm incorporates a digital camera at a distal end, the camera being maneuverable via cables in the scope arm, the scope arm being operatively connectable at a proximal end to an endoscope functional module enabling operation of the camera.

A thoracoscopic surgical port assembly in accordance with the present invention comprises (a) a downwardly tapering, substantially flexible, upper or proximal part, and (b) an upwardly tapering, substantially flexible lower or distal part connected to the upper or proximal part. The lower or distal part is extendable in between the ribs of a patient into a pleural space. A substantially rigid ring-like structure is disposed proximate a junction between the upper or proximal part and the lower or distal part. The ring structure is locatable, during use of the port assembly, on top of a patient's ribs. A flexible membrane is provided proximate the ring structure, the membrane having a plurality of openings for passage of the instruments.

A surgical port assembly comprises, in accordance with another embodiment of the present invention, a rigid mounting ring, a body member and a cannula unit. The ring is disposable on and releasably attachable a patient's skin surface. The body member is attachable to the ring to depend downwardly therefrom through an incision in the patient's skin surface to facilitate deployment of instruments in the patient via the incision. The body member has an outer side facing away from the patient and an inner side facing inwardly of or towards the patient's skin surface during a surgical procedure. The body member is rotatably attachable to the ring for turning about an axis oriented perpendicularly to a plane defined by the ring. The cannula unit is attachable to the body member and carries a plurality of cannulas.

Yet another surgical port assembly in accordance with the present invention comprises a body attachable to a patient at an incision in a skin surface of the patient to facilitate deployment of instruments in the patient via the incision, the body having an outer side facing away from the patient and an inner side facing inwardly of or towards the patient's skin surface during a surgical procedure. The port assembly also comprises a cannula unit including an elastomeric dome-shaped base and a plurality of upwardly extending tubular members or cannulas each provided with a cap housing a plurality of seals.

BRIEF DESCRIPTION OF THE DRAWINGS

FIG. 2 is a schematic cross-sectional view of the trocar or port assembly of FIG. 1, showing the skirt in a free depending configuration.

FIG. 3 is a schematic cross-sectional view of the trocar or port assembly of FIGS. 1 and 2, showing a dome with finger or seal members attached to a body member in the port assembly.

FIG. 4 is a schematic longitudinal cross sectional view of another trocar or surgical port assembly in accordance with the present invention, showing a trocar body with an apertured plate therein.

FIG. 5 is a top plan view of the plate of FIG. 4, showing a pair of openings.

FIG. 6 is a schematic longitudinal cross-sectional view of a modified trocar or surgical port assembly in accordance with the present invention, showing a trocar body with a perforated plate therein.

FIG. 7 is a top plan view of the trocar or surgical port assembly of FIG. 6, showing three instrument ports.

FIG. 8 is a partial schematic cross-sectional view, on a larger scale, of the modified trocar or surgical port assembly of FIGS. 6 and 7.

FIG. 9 is a partial cross-sectional view taken along line IX-IX in FIG. 6.

FIG. 10 is a schematic longitudinal cross-sectional view of another modified trocar or surgical port assembly in accordance with the present invention, largely similar to the port assembly of FIGS. 6-8.

FIG. 11 is a top plan view of the trocar or surgical port assembly of FIG. 10, showing three instrument ports.

FIG. 12 is a partial schematic cross-sectional view, on a larger scale, of the modified trocar or surgical port assembly of FIGS. 10 and 11.

FIG. 15 is a schematic longitudinal cross-sectional view of a further trocar or surgical port assembly in accordance with the present invention.

FIG. 16 is a top plan view of the trocar or surgical port assembly of FIG. 15, showing three instrument ports and an insufflation port. The cross-sectional view of FIG. 15 is taken along line XV-XV in FIG. 16.

FIG. 17 is a partial cross-sectional view, on a larger scale, of a detail XVII of FIG. 15.

FIG. 22 is a schematic side elevational view, partially in cross-section, of a further trocar or surgical port assembly in accordance with the present invention, showing a skirt in a collapsed insertion configuration.

FIG. 23 is partially a side elevational view similar to FIG. 22, showing the skirt in an expanded use configuration.

FIG. 37 is a schematic top perspective view of yet another trocar or port assembly in accordance with the present invention.

FIG. 38 is a longitudinal cross-sectional view of the port assembly body member of FIG. 37.

FIG. 39 is a side elevational view of the port assembly of FIGS. 37 and 38.

FIG. 40 is a perspective view of a lower portion of the port assembly of FIGS. 37-39, showing multiple insufflation port elements.

FIG. 45 is a schematic top perspective view of a three-fingered obturator, in accordance with the present invention, exemplarily for use in deploying the trocar or port assembly of FIGS. 37-40 or FIGS. 41-44 in a patient at the onset of a minimally invasive laparoscopic or thoracoscopic surgical procedure.

FIG. 46 is a side elevational view of the obturator of FIG. 45.

FIG. 46 is a top plan view of the obturator of FIGS. 45 and 46.

DETAILED DESCRIPTION

Figure 1:
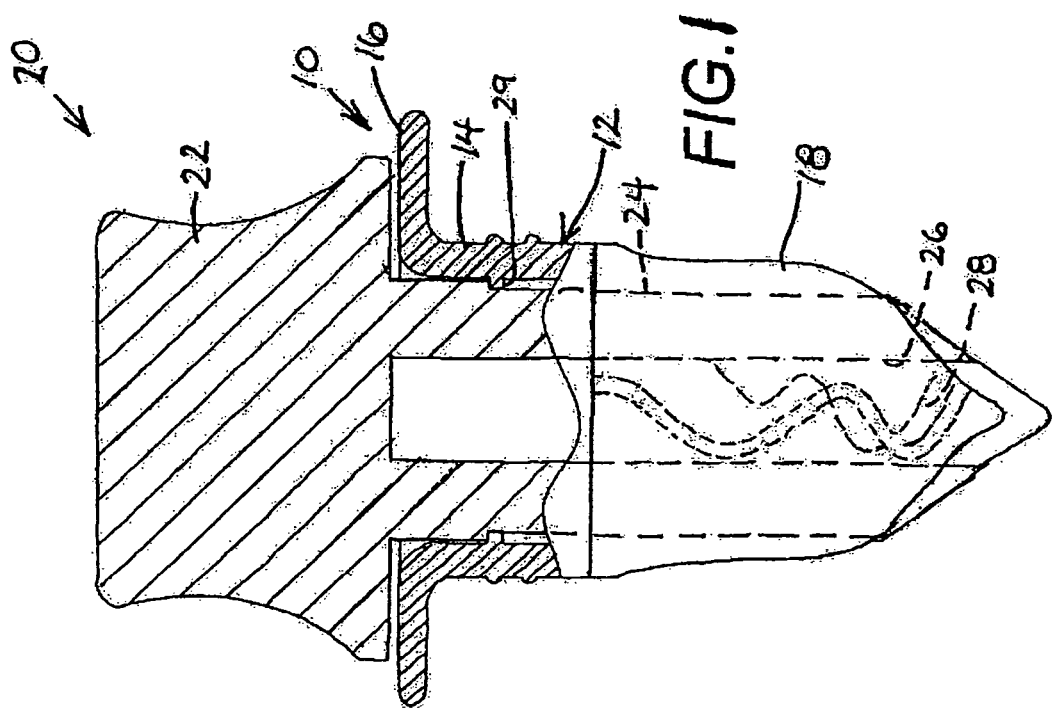
FIG. 1 is partially a schematic side elevational view and partially a schematic longitudinal cross-sectional view of a trocar or surgical port assembly in accordance with the present invention, showing a skirt folded into an obturator for deployment.

As depicted in FIG. 1, a trocar or surgical port assembly 10 useful for laparoscopic or thoracoscopic surgery includes a rigid annular trocar body 12 having a cylindrical portion 14 and a circular flange 16 at a proximal or outer end of the cylindrical portion. Surgical port assembly 10 further includes a fabric or elastomeric skirt 18 attached to a distal end of cylindrical portion 14. An obturator 20 includes a knob or handle 22 and a rigid insertion portion 24 slidably insertable through cylindrical portion 14 of trocar body 12. Rigid insertion portion 24 is provided with a longitudinal slot 26 into which a portion 28 of skirt 18 is folded and secured for facilitating deployment of the port assembly at the onset of a minimally invasive surgical procedure. After insertion of the assembly into an incision, obturator 20 is removed, freeing the skirt, as shown in FIG. 2. Subsequently, a pneumoperitoneum maintenance component 30 (FIG. 3) is attached to trocar body 12 for enabling the passage of instrument shafts through port assembly 10 and into a patient. Cylindrical portion 14 of trocar body 12 is formed internally with an annular rib or a plurality of inwardly extending nubs 29 defining a shoulder on which obturator 20 and component 30 alternatively rest.

Component 30 comprises an elastomeric dome-shaped base 32 and a plurality of upwardly extending tubular members or cannulas 34-36 each provided with a cap 38 housing a plurality of seals (not shown). These seals include a valve (e.g., a tricuspid valve) to prevent air leakage when no instrument is inserted through the tubular member or cannula 34-36. The seals further include an instrument seal exemplarily in the form of a resilient ring or bead fixed to the internal wall of the cannula 34-36 or respective cap 38. Upon insertion of an instrument shaft through a cannula 34-36, the ring or bead hugs the instrument and prevents or minimizes the leakage of insufflation gas. Additional ring or other seals may be incorporated, particularly where the ring or bead seals are provided along a flexible portion of a tubular port member or cannula 34-36. The multiple seals prevent loss of pneumoperitoneum through a cannula 34-36 when an instrument extending therethrough is being manipulated during a procedure.

Generally, in a laparoscopic operation, one of the fingers or cannulas 34-36 receives a laparoscope, while laparoscopic instrument shafts traverse the other two. All three cannulas 34-36 extend away from trocar body 12 only on an outer or upper side thereof, facing away from a patient during a surgical procedure. The underside of the trocar body 12 is free of cannulas. One of the fingers or cannulas 36 is provided with a luer fitting 40 for enabling insufflation of a patient's abdominal cavity during laparoscopic surgery. The fitting is not needed in many thoracoscopic procedures.

Dome-shaped base 32 is provided along a lower periphery with a sealing ring 42 that engages rib or shoulder 29 on cylindrical portion 14. Sealing ring 42 has a sliding engagement with an inner surface (not labels) of cylindrical portion 14 to facilitate a rotation of component 30 about an axis 46 of body member 12. Along an outer surface (not designated), cylindrical portion 14 is formed with a plurality of outwardly extending circumferential ribs or beads 44 for inhibiting slippage in an incision.

As depicted in FIGS. 4 and 5, a surgical port assembly 50 comprises an annular body 52 attachable to a patient at an incision in a skin surface of the patient to facilitate deployment of instruments in the patient via the incision. More particularly, annular body 52 includes a cylindrical insert portion 54 and a flange 56 surrounding a proximal (closer to the surgeon) or outer end of the cylindrical insert portion. Insertion portion 54 is provided along an outer surface with a plurality of longitudinally spaced circular beads 58 and along an inner surface with a circular shoulder 60 (or at least three inwardly extending nubs defining a ledge). Shoulder 60 supports a rigid plate 62 formed with an instrument opening 64 and a scope opening 66. Plate 62 may be rotatably or rigidly secured to cylindrical insert portion 54 of annular body 52. An ancillary second plate 68 having a dome shape is rotatably and removably attached to the main plate 62 over opening 64. Ancillary plate 68 carries a pair of integrally formed tubular members or cannulas 70 made of a flexible material and provided at free ends with respective sealing caps 72. A third tubular sealing member or cannula 74 is attached to main plate 62 over scope opening 66 for enabling the introduction of a distal end portion of a laparoscope or other endoscope into a patient through port assembly 50. Scope cannula 74 has a luer fitting 76 for insufflation purposes. Tubular fingers or cannulas 70 and 74 extend in an upper direction away from plates 62 and 68 and are disposed only on an upper or outer side thereof, facing away from a patient during a surgical procedure. The lower or inwardly facing side of port assembly 50 is free of cannula parts.

Plate 68 is rotatably disposed in or at opening 64 for turning about an axis 78 preferably substantially parallel to a main axis 79 of port assembly 50.

Tubular fingers or cannulas 70 and 74 are flexible at least at a point of attachment to plates 68 and 62, respectively, enabling a pivoting (about a transverse axis) and/or a swiveling (about a longitudinal axis) of surgical instruments (or an endoscope) inserted through the tubular fingers or cannulas 70, 74. Fingers or cannulas 70, 74 are each provided with at least one seal for maintaining pneumoperitoneum when a surgical instrument shaft longitudinally traverses such finger or cannula and at least one seal for maintaining pneumoperitoneum in the absence of a surgical instrument shaft longitudinally traversing such finger or cannula.

FIGS. 6-8 illustrate a modified version 80 of the trocar or surgical port assembly of FIGS. 4 and 5. Surgical port assembly 80 comprises an annular body 82 attachable to a patient at an incision in a skin surface of the patient to facilitate deployment of instruments in the patient via the incision. More particularly, annular body 82 includes a cylindrical insert portion 84 and a flange 86 surrounding a proximal or outer end of the cylindrical insert portion. Insertion portion 84 is provided at a distal or inner end with an annular slot 88 that receives en edge of a skirt 90. Skirt 90 is an elastomeric annular or slotted web member in which a plurality of longitudinal support wires 92 are embedded (see FIG. 9). At least some of the wires 92 extend generally parallel to a longitudinal axis 94 of trocar body 82. Wires 92 serve to form skirt 90 into an expanded funnel shape upon deployment of the surgical port assembly 80 in a patient.

Trocar body 82 is formed along an inner surface with a ledge or plate 96 defining an instrument opening 98 and a scope opening 100. Plate 96 is rigidly secured to cylindrical insert portion 84 of annular body 82. An ancillary second plate or disk 102 is rotatably and removably attached to the main plate 96 over opening 98. A locking ring 104 may be provided (FIG. 8) for releasably holding plate or disk 102 to plate 96 at opening 98. Ancillary plate or disk 102 carries a pair of tubular fingers or cannulas 106 made of a flexible material and provided at free ends with respective sealing caps 108. Fingers or cannulas 106 may be removably attached to plate or disk 102. To that end, plate or disk 102 may be formed with a pair of outwardly extending sleeves 110 (FIG. 8) insertable into tubular fingers or cannulas 106. A third tubular sealing finger or cannula 112 is attached to main plate 96 over scope opening 100 for enabling the introduction of a distal end portion of a laparoscope or other endoscope into a patient through port assembly 80. Scope cannula 112 may have a luer fitting (not shown) for insufflation purposes. Tubular fingers or cannulas 106 and 112 extend in an upper direction away from plates 96 and 102 and are disposed only on an upper or outer side thereof, facing away from a patient during a surgical procedure. The lower or inwardly facing side of port assembly 80 is free of cannula parts.

Plate or disk 102 serves as a cannula carrier that is rotatably disposed in or at opening 98 for turning about an axis 114 preferably substantially parallel to main axis 94 of port assembly 80.

Tubular fingers or cannulas 106 and 112 are flexible at least at a point of attachment to plates 102 and 96, respectively, enabling a pivoting (about a transverse axis) and/or a swiveling (about a longitudinal axis) of surgical instruments (or an endoscope) inserted through the ports formed by tubular fingers or cannulas 106, 112. Fingers or cannulas 106, 112 are each provided with at least one seal for maintaining pneumoperitoneum when a surgical instrument shaft longitudinally traverses such finger or cannula and at least one seal for maintaining pneumoperitoneum in the absence of a surgical instrument shaft longitudinally traversing such finger or cannula.

FIG. 6 shows an obturator shaft 118 and skirt 90 folded and tucked into a slot along shaft 118. A knob (not shown) at the proximal or outer end of obturator shaft 118 is pushed to release skirt 90 from obturator shaft 118. The obturator is then pulled out and discarded. A release and discard safety tab is shown at 120.

FIGS. 10-12 depict a port assembly 80' that is a modified version of port assembly 80 of FIGS. 6-8. The same reference numerals are used in FIGS. 10-12 to designate the same parts as shown in FIGS. 6-8. Instead of integral or unitary main plate 96, port assembly 80' has a removable main plate 122 that is releasably secured to cylindrical insertion portion 84 via a plurality of spring-loaded detents 124. Main plate 122 sits on an inwardly extending shoulder 126 (or series of nubs) and is held thereto in a snap lock fit by the plurality of spring-loaded detents 124.

Figure 14:
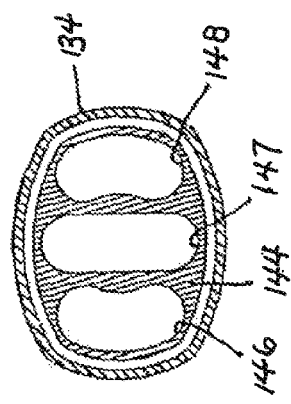
FIG. 14 is a cross-sectional view taken along line XIV-XIV in FIG. 13.
Figure 13:
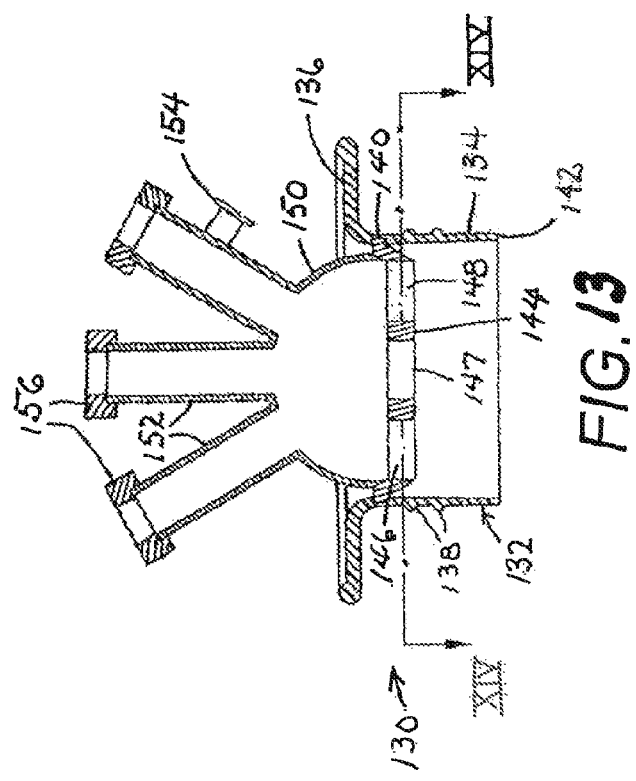
FIG. 13 is a schematic longitudinal cross-sectional view of another trocar or surgical port assembly in accordance with the present invention.

As shown in FIGS. 13 and 14, another trocar or surgical port assembly 130 comprises an annular body 132 attachable to a patient at an incision in a skin surface of the patient to facilitate deployment of instruments in the patient via the incision. Annular body 132 includes a substantially oval insert portion 134 and a flange 136 at a proximal (closer to the surgeon) or outer end of the cylindrical insert portion. Insertion portion 134 is provided along an outer surface with a plurality of longitudinally spaced circular beads 138 and along an inner surface with a substantially annular or endless groove 140. A skirt (not shown) may be attached to an inner or distal end 142 of cylindrical insert portion 134.

Groove 140 receives an outer end of a rigid support or base plate 144 provided with three slots 146-148. Central slot 147 is intended for insertion of a laparoscope in an abdominal operation, while lateral slots 146 and 148 are intended for the passage of instrument shafts. An ancillary second plate 150 made of elastomeric material having a dome shape is attached to the support or base plate 144 over opening slots 146-148. Base plate 144 and ancillary plate 150 have a generally elongate or oval cross-section, as seen in FIG. 14. Ancillary plate 150 carries three integrally formed tubular members or cannulas 152 (one provided with a luer fitting 154 for insufflation) made of flexible elastomeric material and provided at free ends with respective sealing caps 156. Tubular fingers or cannulas 152 extend in an upper direction away from plates 144 and 150 and are disposed only on an upper or outer side thereof, facing away from a patient during a surgical procedure. The lower or inwardly facing side of port assembly 130 is free of cannula parts.

Tubular fingers or cannulas 152 are flexible at least at a point of attachment to plate 150, enabling a pivoting (about a transverse axis) and/or a swiveling (about a longitudinal axis) of surgical instruments (or an endoscope) inserted through the tubular fingers or cannulas. Fingers or cannulas 152 are each provided (for instance, in caps 156) with at least one seal for maintaining pneumoperitoneum when a surgical instrument shaft longitudinally traverses such finger or cannula and at least one seal for maintaining pneumoperitoneum in the absence of a surgical instrument shaft longitudinally traversing such finger or cannula.

As shown in FIGS. 15-17, a further trocar or surgical port assembly 160 comprises an annular body 162 attachable to a patient at an incision in a skin surface of the patient to facilitate deployment of instruments in the patient via the incision. Annular body 162 includes a cylindrical insert portion 164 and a flange 166 at a proximal or outer end of the cylindrical insert portion. A skirt (not shown) may be attached to an inner or distal end 168 of cylindrical insert portion 164.

A groove 170 provided in a widened section 172 of cylindrical insertion portion 164 permanently receives an outer periphery of a perforated support or base plate 174. Plate 174 may be made of a rigid (e.g. metallic) or elastomeric material and is formed with three instrument openings 176 and a smaller insufflation opening 178. Three elastomeric tubular fingers or cannulas 180 are connected to plate 174 and communicate with respective openings 176. In the case of an elastomeric base plate 174, cannulas 180 are formed integrally therewith. Tubular fingers or cannulas 180 are flexible at least at a point of attachment to plate 174, enabling a pivoting and/or swiveling of surgical instruments (or an endoscope) inserted through the tubular fingers or cannulas. Fingers or cannulas 152 are each provided with at least one inner ring seal 182 for maintaining pneumoperitoneum when a surgical instrument shaft longitudinally traverses such finger or cannula and at least one seal (e.g., a tricuspid valve at a lower end 184) for maintaining pneumoperitoneum in the absence of a surgical instrument shaft longitudinally traversing such finger or cannula.

Tubular fingers or cannulas 180 serve to seal the abdominal cavity during pneumoperitoneum and further serve to protect the patient's internal tissues, such as the abdominal wall tissues. Fingers or cannulas 180 extend only downwardly or inwardly away from support or base plate 174, on the inner side of the trocar body 162.

Figure 19:
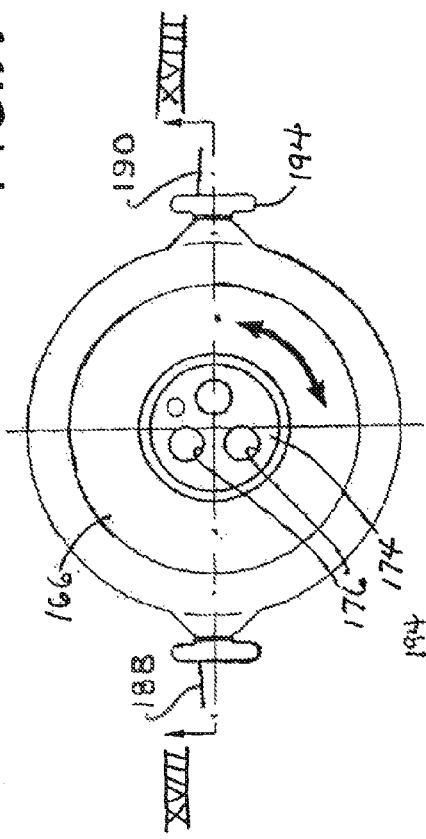
FIG. 19 is a top plan view of the trocar or surgical port assembly and mounting ring of FIG. 16. The cross-sectional view of FIG. 18 is taken along line XVIII-XVIII in FIG. 19.
Figure 18:
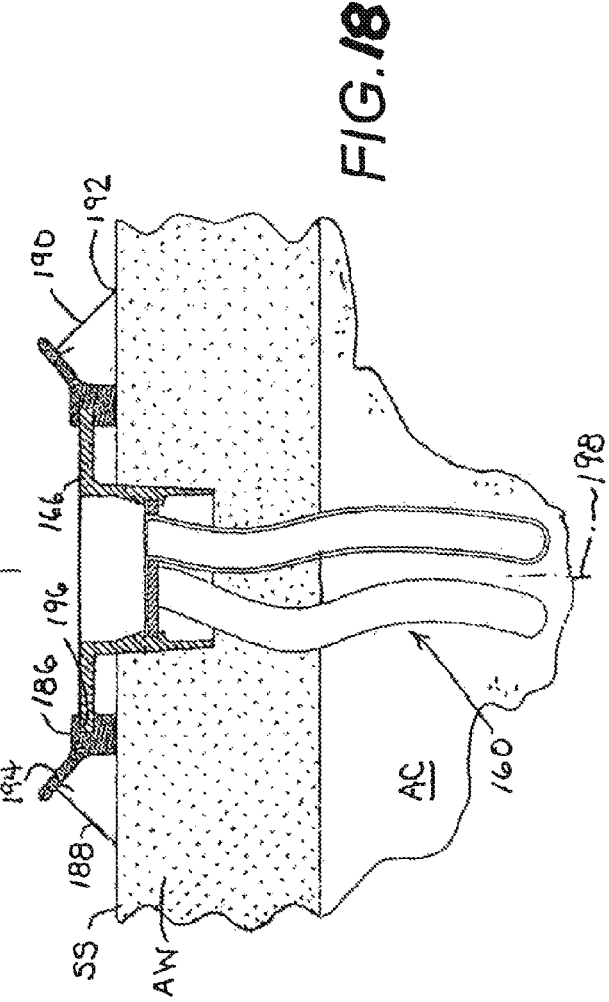
FIG. 18 is a schematic longitudinal cross-sectional view of the trocar or surgical port assembly of FIGS. 15-17, showing the port assembly rotatably supported via a mounting ring on a patient's abdomen.

FIGS. 18 and 19 show a scheme for deploying the port assembly 160 of FIGS. 15-17. A rigid mounting ring 186 is disposed on a skin surface SS over a patient's abdominal cavity AC and attached to the skin via sutures 188 and 190. Sutures 188 and 190 are sewn at one end 192 to the patient and are tied at opposing ends to respective dual-hook members 194 that are upwardly inclined from mounting ring 186. An outer periphery (not labeled) of flange 166 is slidably inserted into an annular groove 196 provided on an inner surface of mounting ring 186. Cylindrical portion 164 of port assembly body 162 depends downwardly into the abdominal wall AW of a patient during a surgical procedure. Fingers or cannulas 180 extend through a portion of abdominal wall AW and into an abdominal cavity AC of the patient. Trocar body 162 may be turned about a longitudinal axis 198 of port assembly 160, while mounting ring 186 remains stationary relative to the patient, to facilitate the manipulation of laparoscopic instruments (not shown) whose shafts are inserted through respective fingers or cannulas 180.

Figure 21:
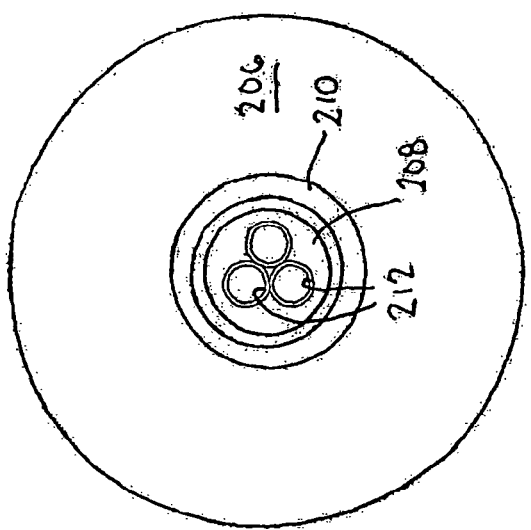
FIG. 21 is a top plan view of the trocar or surgical port assembly of FIG. 20, showing three instrument ports. The cross-sectional view of FIG. 20 is taken along line XX-XX in FIG. 21.
Figure 20:
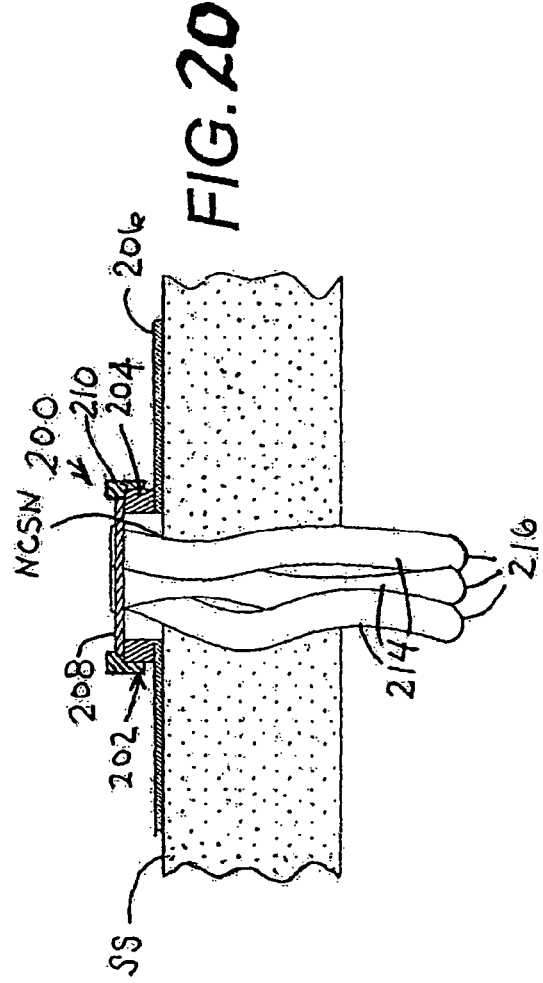
FIG. 20 is a schematic longitudinal cross-sectional view of a further trocar or surgical port assembly in accordance with the present invention, showing the port assembly deployed in an abdominal wall of a patient.

FIGS. 20 and 21 depict an alternative surgical access port assembly 200 comprising an annular body 202 attachable to a patient at an incision NCSN in a skin surface SS of the patient to facilitate deployment of instruments in the patient via the incision. Annular body 202 includes a mounting ring 204 fixed to an adhesive pad 206 that in turn is releasably adhered to skin surface SS about incision NCSN. Port assembly 200 further comprises a rigid plate 208 rotatably or rigidly secured to mounting ring 204 via a locking ring 210. Plate 208 may be made of a rigid (e.g. metallic) or elastomeric material and is formed with three instrument openings 212 and a smaller insufflation opening (not shown). Three elastomeric tubular fingers or cannulas 214 are connected to plate 208 and communicate with respective openings 212. In the case of an elastomeric base plate 208, cannulas 214 are formed integrally therewith. Tubular fingers or cannulas 214 are flexible at least at a point of attachment to plate 208, enabling a pivoting and/or swiveling of surgical instruments (or a scope) inserted through the tubular fingers or cannulas. Fingers or cannulas 214 are each provided with at least one inner ring seal (not sown) for maintaining pneumoperitoneum when a surgical instrument shaft longitudinally traverses such finger or cannula and at least one seal (e.g., a tricuspid valve at a lower end 216) for maintaining pneumoperitoneum in the absence of a surgical instrument shaft longitudinally traversing such finger or cannula.

Tubular fingers or cannulas 214 serve to seal the abdominal cavity AC during pneumoperitoneum in a laparoscopic procedure and further serve to protect the patient's internal tissues, such as the tissues of abdominal wall AW. Fingers or cannulas 214 extend only downwardly or inwardly away from support or base plate 208, on the inner side of the body 202. Fingers or cannulas 214 can accommodate instrument shafts that are fully flexible as well as instruments shaft that have preformed rigid shapes, including C-shaped and S-shaped portions.

As illustrated in FIGS. 22 and 23, another trocar or surgical port assembly 220 comprises an annular body 222 attachable to a patient at an incision in a skin surface of the patient to facilitate deployment of instruments in the patient via the incision. Annular body 222 includes a cylindrical insert portion 224 and a flange 226 at a proximal or outer end of the cylindrical insert portion. A skirt 228 is attached to an inner or distal end 230 of cylindrical insert portion 224. Skirt 228 includes a flexible web 232 and a stent wire 234 attached to the web (e.g., inserted into a cavity or pocket, not shown, formed in the web). Wire 234 has a zig-zag or snaking configuration and serves to spring-bias web 232 into a conical or funnel-shaped open configuration shown in FIG. 23. Trocar or surgical port assembly 220 additionally comprises a purse-string closure element 236 disposed about a distal or free end of skirt 228 for the skirt in a closed or pointed insertion configuration (FIG. 22) in opposition to the opening force exerted by wire 234. Purse string closure element 236 is connected to a deployment knob or button 237 via an obturator shaft 238. Upon insertion of folded or pointed skirt 228 (FIG. 22) and cylindrical insert portion 224 into an abdominal wall of a patient, the user actuates knob or button 237 to release purse-string closure element 236, thereby enabling the opening of skirt 228 into the opened funnel-shaped use configuration (FIG. 23) under the biasing force exerted by wire 234.

Trocar or surgical port assembly 220 of FIGS. 22 and 23 comprises additional structure described hereinabove with reference to FIGS. 10-12. The same reference numerals are used in FIGS. 10-12 and 22, 23 to designate identical structures. In FIGS. 22 and 23, fingers or cannulas 106 and 112 are additionally shown with sealing structures 239.

Figure 25:
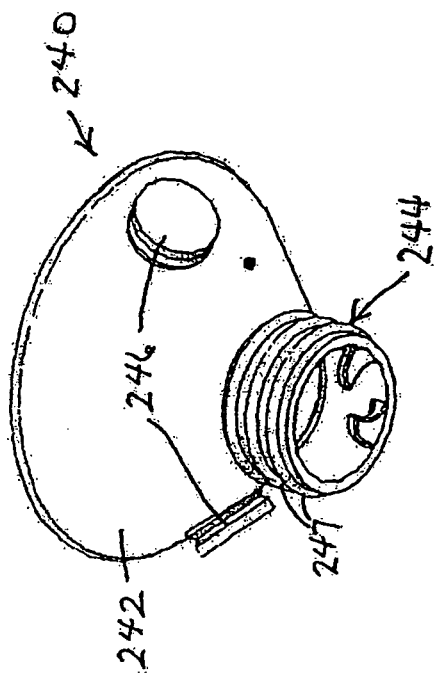
FIG. 25 is a schematic perspective bottom view of the surgical port assembly of FIG. 24.
Figure 24:
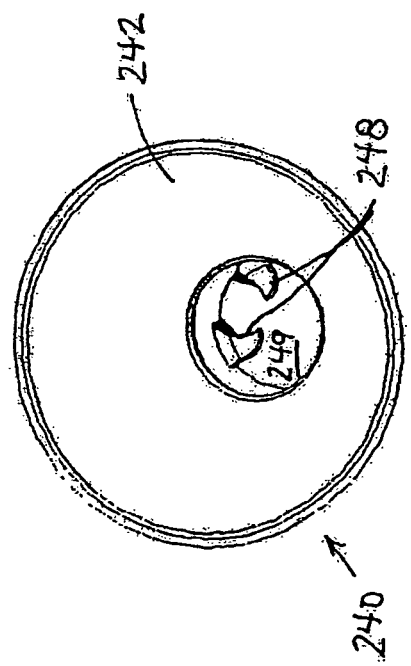
FIG. 24 is a schematic perspective top view of another surgical port assembly in accordance with the present invention.

As shown in FIGS. 24 and 25, another trocar port assembly 240 comprises a body member (not separately designated) including a funnel-shaped upper or proximal portion 242 and a cylindrical lower or distal portion 244. Upper or proximal portion 242 is provided along a conical outer surface (not separately labeled) with a plurality of laterally grooved cylindrical posts 246 for receiving tie-down sutures (not shown) to anchor the trocar port assembly 240 to a patient at an incision site (such as the umbilicus). Cylindrical portion 244 is provided along an outer surface with a plurality of annular ribs 247 for enhancing a seating of the cylindrical portion in an incision. On an inner surface and at a bottom or distal end, cylindrical portion 244 is provided with a pair of opposing generally arcuate teeth or prongs 248 that serve to hold or lock a laparoscope or other endoscope in a position at the outlet end of cylindrical portion 244. During a surgical procedure, laparoscopic instrument shafts (not shown) longitudinally traverse flexible fingers or cannulas (not shown) that pass through an open area 249 in the bottom or distal end of cylindrical portion 244.

Figure 26:
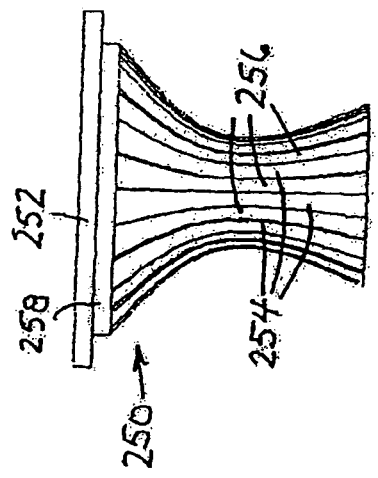
FIG. 26 is a schematic top perspective view of an expandable skirt utilizable in a surgical port assembly in accordance with the present invention.
Figure 28:
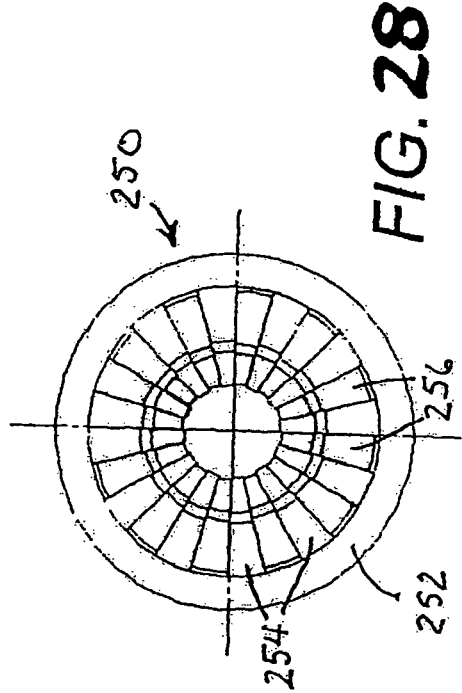
FIG. 28 is a top view of the skirt of FIGS. 26 and 27.
Figure 27:
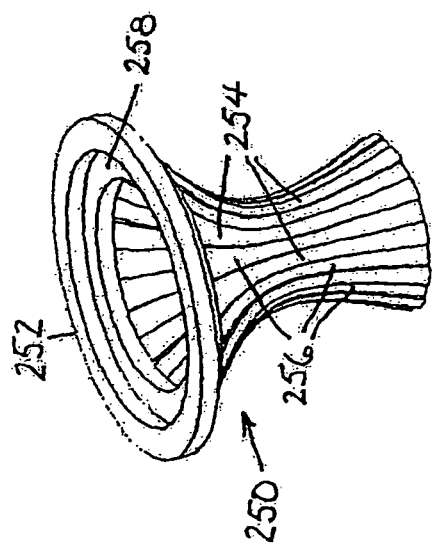
FIG. 27 is a side elevational view of the skirt of FIG. 26.
Figure 29:
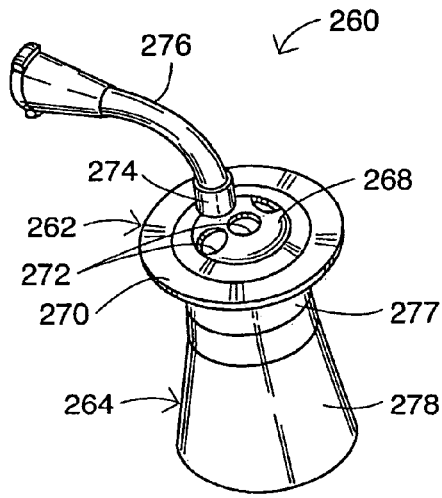
FIG. 29 is a schematic top perspective view of an elastomeric two-shot domed trocar or port assembly in accordance with the present invention.
Figure 30:
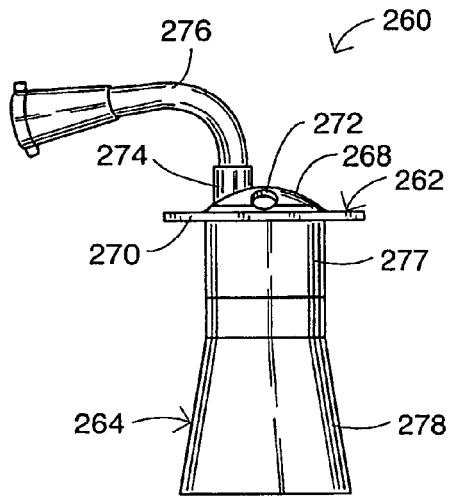
FIG. 30 is a side elevational view of the port assembly of FIG. 29.
Figure 31:
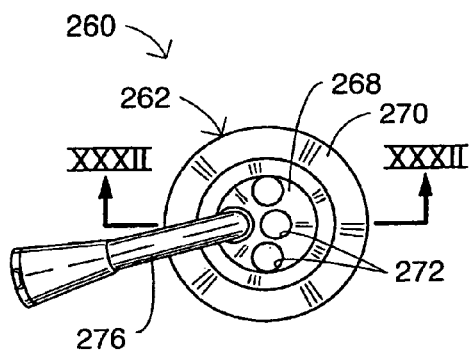
FIG. 31 is a top plan view of the port assembly of FIGS. 29 and 30.
Figure 32:
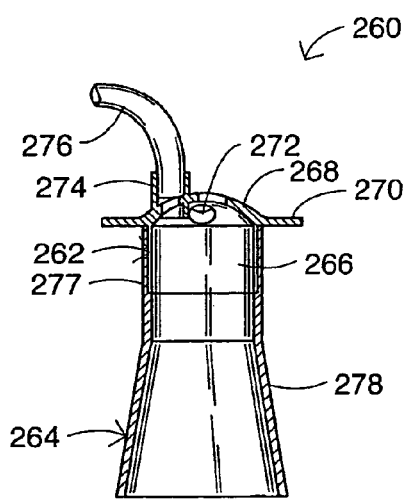
FIG. 32 is a longitudinal cross-sectional view taken along line XXXII-XXXII in FIG. 31.
Figure 33:
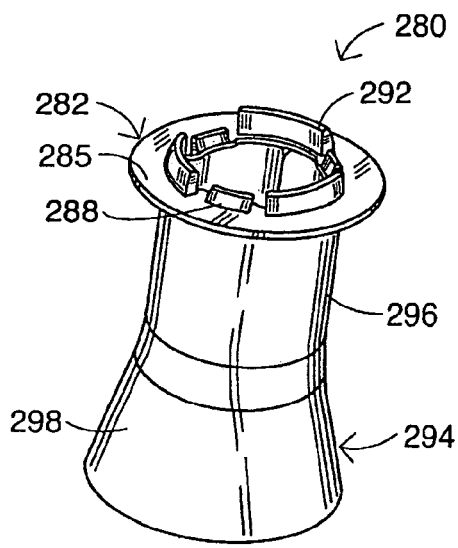
FIG. 33 is a schematic top perspective view of a body member of a hinged trocar or port assembly in accordance with the present invention.
Figure 34:
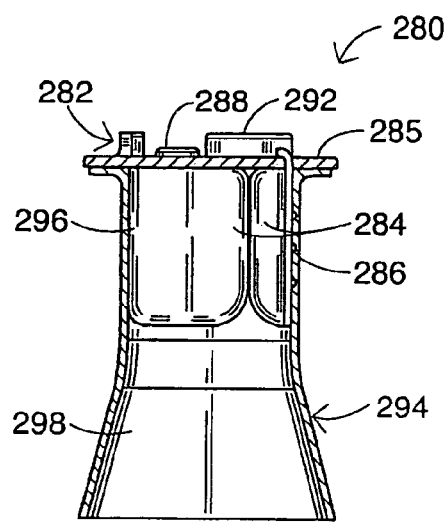
FIG. 34 is a longitudinal cross-sectional view of the port assembly body member of FIG. 33, showing the body member together with a skirt.
Figure 35:
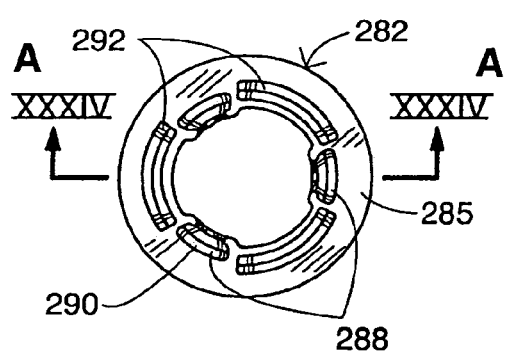
FIG. 35 is a top plan view of the port assembly of FIG. 33. The longitudinal cross-sectional view of FIG. 34 is taken along line XXXIV-XXXIV in FIG. 35.
Figure 36:
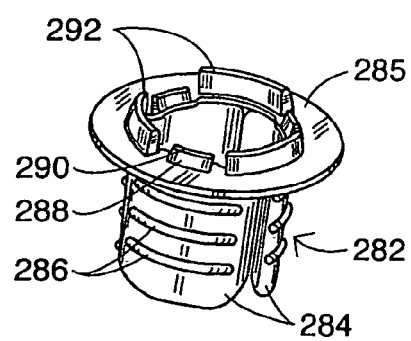
FIG. 36 is a perspective view of the port assembly of FIGS. 34 and 35.

FIGS. 26-28 illustrate a trocar skirt 250 comprising a rigid support ring 252, a multiplicity of substantially rigid strips or bands 254 connecting to one another via elastomeric sections 256. Rigid strips 254 are arranged in an annular configuration and are concave in a radially outward direction. Elastomeric sections 256 may be angularly or circumferentially spaced portions of a single web or separate strips. Rigid strips or bands 254 are pivotably attached at an upper or proximal end to a mounting ring 258 in turn fastened to support ring 252. The pivotable attachment of strips or bands 254 to mounting ring 258 may take the form of a so-called living hinge, for example, wherein mounting ring 258 and strips or bands 254 are integrally made of a substantially rigid polymeric material that is sufficiently thin at connecting points to enable a pivoting and/or swiveling motion.

Elastomeric sections 256 of trocar skirt 250 are capable of stretching sufficiently to permit a full range of instrument and scope motion during a surgical procedure while protecting a patient's abdominal tissues. Trocar skirt 250 has a corset shape, with a waist diameter that may alternately increase and decrease during instrument manipulation.

Trocar skirt 250 is attached to an underside of a trocar assembly such as the port assemblies described hereinabove with reference to FIGS. 1-14.

As shown in FIGS. 29-32, a trocar or surgical port assembly 260 comprises an upper or proximal body 262 and a skirt 264. Body 262 is made of a flexible elastomeric material and includes a cylindrical portion 266, a dome 268 and a circumferential or annular disk-shaped flange 270. Dome 268 is formed with a plurality of openings 272 for the passage of laparoscopic or thoracoscopic instrument shafts (not shown) and a laparoscope or endoscope (not shown). Openings 272 are formed with slit-type seals for preventing the loss of pneumoperitoneum both when instruments shafts pass through the openings and when there are no instruments traversing the openings. Dome 268 is further formed with a tubular stub 274 that receives a distal end of an insufflation tube 276. Skirt 264 includes a cylindrical proximal sleeve 277 that fits over and is functionally connected to cylindrical portion 266. Skirt 264 further includes a resilient frusto-conical portion 278 that is folded and preferably held to an obturator shaft during insertion through an incision.

FIGS. 33-36 depict a trocar or surgical port assembly 280 including a body 282 having a cylindrical portion (not separately designated) formed by a plurality of cylindrical sections or flaps 284 swingably connected to a ring-shaped base member 285 in the nature of a flange to the cylindrical portion. Flaps 284 are made of at least a substantially rigid material and each include plural longitudinally spaced arcuate ribs 286 along a respective outer surface. Flaps 284 each have a hinge projection 288 that is inserted through a slot 290 in base member 285. Projections 288 are hooked, to prevent a disassociation of flaps 284 from base member 285. Base member 285 is provided with a plurality of upwardly or proximally extending arcuate flange sections 292 that are received into a distal or lower end of a cylindrical body of a flexible-cannula port member such as the domed members of FIGS. 3 and 13, 14.

Surgical port assembly 280 further comprises a skirt 294 including a cylindrical proximal sleeve 296 that fits over flaps 284 and is thereby functionally connected to body 282. Skirt 294 further includes a resilient frusto-conical portion 298 that is folded and preferably held to an obturator shaft during insertion through an incision.

As shown in FIGS. 37-39, yet another trocar port assembly 300 comprises a body member (not separately designated) including a funnel-shaped upper or proximal portion 302 and a cylindrical lower or distal portion 304. Upper or proximal portion 302 is provided along a circular rim 306 with a plurality of suture anchors 308 in the form of substantially flat, generally triangular upwardly inclined posts for receiving tie-down sutures (not shown) to anchor the trocar port assembly 300 to a patient at an incision site (such as the umbilicus). Upper or proximal portion 302 is additionally provided along circular rim 306 with a plurality of rectangular recesses 310 for receiving mating projections on an obturator (see FIGS. 45-47). Cylindrical portion 304 is provided along an outer surface with a helical thread or one or more outwardly extending ribs 312 for enhancing a sealed seating of the cylindrical portion in an incision.

Port assembly 300 further includes, at a bottom or distal end (not separately enumerated) of cylindrical portion 304, an elastomeric "pants" member 314 illustrated separately in FIG. 40. Pants member 314 includes a cannula carrier 316 and cannula members in the form of three elastomeric legs or downwardly depending fingers 318, 319, 320 that are each provided with an inwardly extending ring seal 322 and a tricuspid seal 324. Leg 320 is dedicated to the passage of a scope (not shown), while the remaining two legs 318, 319 have a wider and deeper entrance space or antechamber 326 allowing an increased range of instrument motion and an easier crossing of the instrument shafts (not shown).

Legs or fingers 318-320 are provided internally with polytetrafluorethylene stiffening tubes 328 that provide strength and rigidity and reduce friction. Stiffening tubes 328 facilitate the withdrawal of laparoscopic instrument shafts (including scopes) by preventing the entrainment of the instrument shafts to the legs or fingers 318-320. Accordingly, stiffening tubes 328 prevent a turning inside-out of legs or fingers 318-320.

Legs, fingers or cannulas 318-320 are flexible in a region of attachment to domed cannula carrier 316, whereby the legs/fingers/cannulas may be temporarily bent into a parallel configuration for insertion into a patient through an incision with the aid of an obturator (see FIGS. 45-47).

As shown in FIG. 40, cannula carrier 316 of pants member 314 includes multiple insufflation ports 330 and 332 providing an option of connecting insufflation hoses (not shown) at a center (330) or a periphery (332).

As depicted in FIGS. 41-44, a similar trocar port assembly 340 comprises a body member 341 including a rigid conical upper or proximal portion 342 and a cylindrical lower or distal portion 344. Upper or proximal portion 342 is provided along a circular rim 346 with a plurality of suture anchors 348 in the form of substantially flat, generally triangular upwardly inclined posts for receiving tie-down sutures (not shown) to anchor the trocar port assembly 340 to a patient at an incision site (such as the umbilicus). Upper or proximal portion 342 is additionally provided along circular rim 346 with a plurality of rectangular recesses 350 for receiving mating projections on an obturator (see FIGS. 45-47). Cylindrical portion 344 is provided along an outer surface with a helical thread or one or more outwardly extending ribs 352 for enhancing a sealed seating of the cylindrical portion in an incision.

Figure 44:
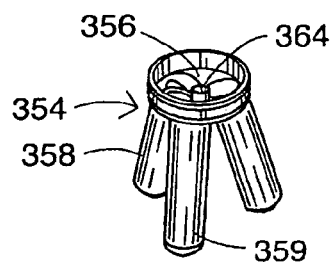
FIG. 44 is a perspective view of a lower portion of the port assembly of FIGS. 40-43, showing multiple insufflation port elements.
Figure 48:
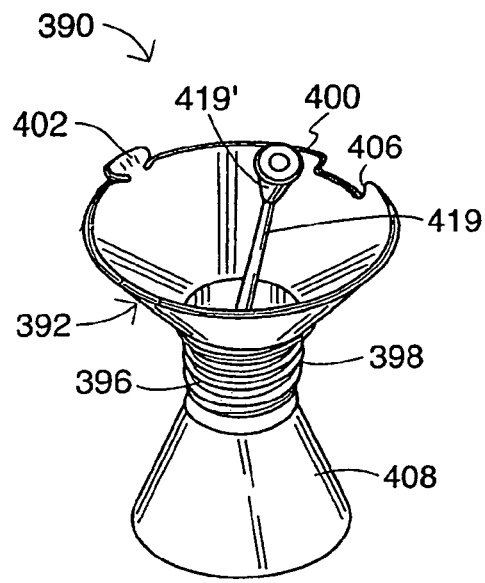
FIG. 48 is a schematic top perspective view of another trocar or port assembly in accordance with the present invention.
Figure 49:
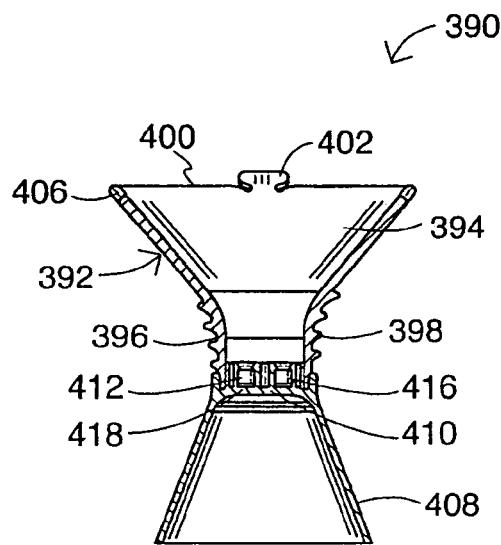
FIG. 49 is a longitudinal cross-sectional view of the port assembly of FIG. 48.
Figure 50:
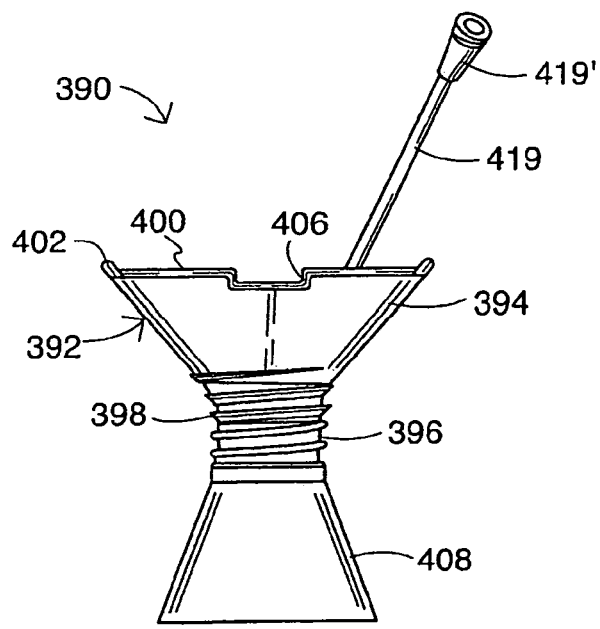
FIG. 50 is a side elevational view of the port assembly of FIGS. 48 and 49.
Figure 51:
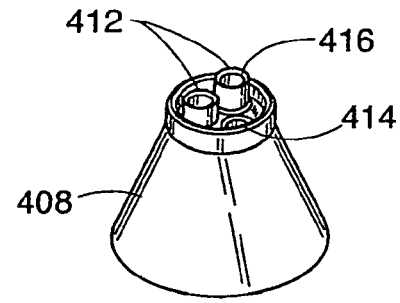
FIG. 51 is a perspective view of a lower portion of the port assembly of FIGS. 40-43, showing multiple insufflation port elements.

Port assembly 340 further includes, at a bottom or distal end (not separately enumerated) of cylindrical portion 344, an elastomeric "pants" member 354 illustrated separately in FIG. 44. Pants member 354 includes a domed cannula carrier 356 and cannula members in the form of three elastomeric legs or downwardly depending fingers 358, 359, 360 that are each provided with (i) a ring seal 322 in the form of an annular bead and (ii) a tricuspid insufflation seal 324. Legs 358-360 are identical and interchangeably used for the passage of a scope (not shown) or surgical instrument shafts (not shown). Legs 358-360 are circumferentially equispaced and outwardly inclined in a mutually flared configuration.

Legs or fingers 358-360 are lined with polytetrafluorethylene stiffening tubes 362 that strengthen and rigidify the major portions of the legs and additionally reduce friction between the instrument shafts and the legs. During the withdrawal of laparoscopic instrument shafts (including scopes) from legs or fingers 358-360, stiffening tubes 362 prevent the entrainment of the instrument shafts to the legs or fingers. Thus, stiffening tubes 362 prevent legs or fingers 358-360 from turning inside out.

Legs, fingers or cannulas 358-360 are flexible in a region of attachment to domed cannula carrier 356, thereby enabling a temporary deformation of the cannulas into a parallel configuration for insertion into a patient through an incision with the aid of an obturator (see FIGS. 45-47). Legs, fingers or cannulas 358-360 are provided at an upper or proximal end with circumferential rind seals 361 and at a lower or distal end 363 with tricuspid seals.

Figure 41:
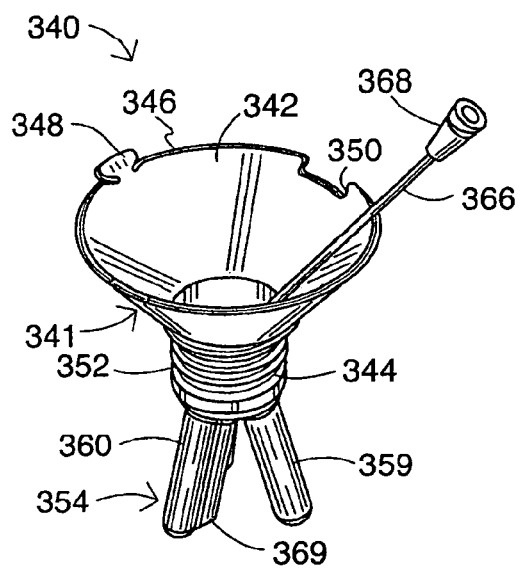
FIG. 41 is a schematic top perspective view of another trocar or port assembly in accordance with the present invention, similar to the trocar or port assembly of FIGS. 37-39.
Figure 42:
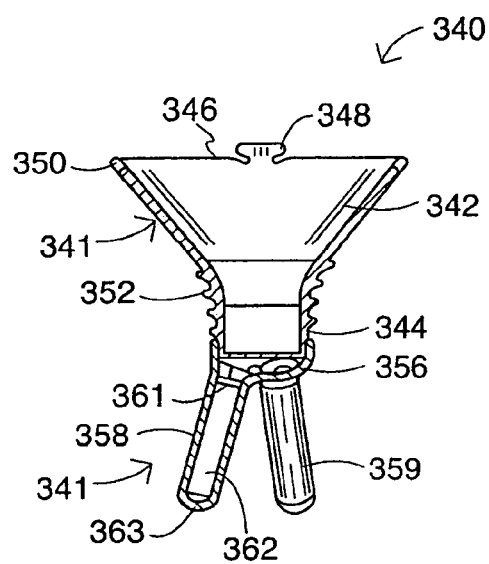
FIG. 42 is a longitudinal cross-sectional view of the port assembly of FIG. 41.
Figure 43:
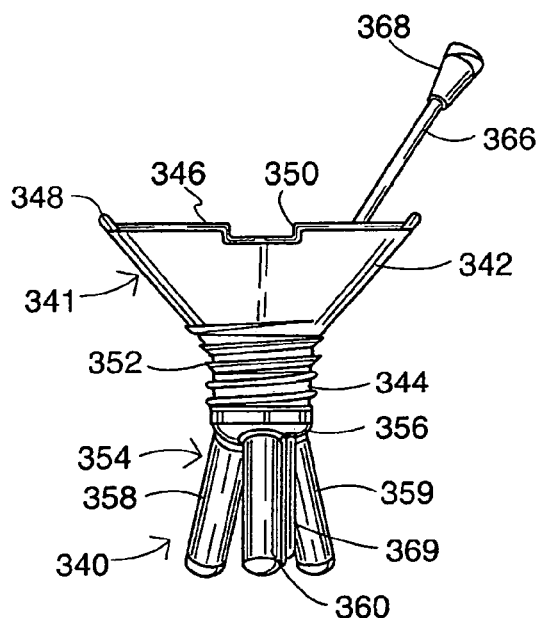
FIG. 43 is a side elevational view of the port assembly of FIGS. 41 and 42.

As depicted in FIG. 44, cannula carrier 356 of pants member 354 may include a central insufflation port 364 with an outlet (not shown) on an outer or distal surface (not separately designated) of domed cannula carrier 356. Alternatively or additionally, as depicted in FIGS. 41 and 43, an insufflation tube 366 with a luer lock 368 may extend through domed carrier 356 and alongside a leg 360, as indicated at 369.

FIGS. 45-47 illustrate an obturator 370 for deployment of a surgical port assembly such as assembly 300 or 340 through a skin surface of a patient. Obturator 370 comprises a disk-shaped body member 372, locking formations 374 in the form of generally rectangular keys projecting radially outwardly from body member 372 and releasably engageable with cooperating locking formations on port assembly 300 or 340, namely rectangular recesses 310 or 350. At least two finger contact surfaces 376 and 378 are provided on body member 372, the finger contact surfaces facing in substantially opposed directions, for enabling manual application of a torque to the body member. In the illustrated embodiment, finger contact surfaces 376 and 378 are formed on respective upstanding tabs (not separately designated) disposed along a diameter of body member 372. Obturator 370 further comprises at least one elongate rigid member 380 extending away from the body member on a side thereof opposite finger contact surfaces 376 and 378, for penetrating through a skin surface of a patient.

In the illustrated embodiment, rigid penetrating member 380 is one of three parallel elongate rigid members 380, 381, 382 extending away from body member 372 on a side thereof opposite finger contact surfaces 376 and 378, for penetrating through a skin surface. Rigid members 380-382 insert into respective downwardly depending tubular leg or finger members 318-320 or 358-360 of port assembly 300 (FIGS. 37-40) or 340 (FIGS. 41-44). Rigid members 380-382 serve to stiffen and hold tubular leg or finger members 318-320 or 358-360 when port assembly 300 or 340 is being deployed at the onset of a minimally invasive surgical procedure, for example, a laparoscopic or thoracoscopic operation.

Disk or body member 372 is formed along a periphery with one or more cutouts 384 serving as insufflation tube exit paths.

Obturator 370 allows for easy insertion of any trocar or port assembly having three distal leg or finger seals. After the trocar or instrument port assembly is in place, the obturator is simply pulled out of the port assembly and the minimally invasive laparoscopic or thoracoscopic procedure can begin.

As shown in FIGS. 48-51, a surgical port assembly 390 comprises a body member 392 that includes a rigid conical upper or proximal portion 394 and a cylindrical lower or distal portion 396. Cylindrical portion 396 is formed along an outer surface with a helical sealing thread or one or more outwardly extending ribs 398.

Upper or proximal portion 394 is provided along a circular rim 400 with a plurality of suture anchors 402 in the form of substantially flat, upwardly inclined posts for receiving tie-down sutures (not shown) to anchor the trocar port assembly 390 to a patient at an incision site (such as the umbilicus). Upper or proximal portion 394 is additionally provided along circular rim 400 with a plurality of rectangular recesses 406 for receiving mating projections or keys 374 on obturator body member 372 (see FIGS. 45-47).

Surgical port assembly 390 further comprises an elastomeric skirt 408 attached to a distal edge of cylindrical portion 396. Skirt 408 provides a protective barrier between laparoscopic instrument shafts (as well as their operative tips) and abdominal wall tissues. At an upper or proximal end, skirt 408 is formed with a transverse membrane 410 provided with a pair of upwardly extending sleeves 412 for receiving laparoscopic instruments. A downwardly extending third sleeve 414 is provided for the passage of a scope. Sleeves 412 and 414 are provided at upper ends with circumferential ring seals 416 engageable with instrument shafts during an operation. In addition, membrane 410 is formed with tricuspid seals 418 at the lower ends of sleeves 412. Sleeve 414 also has a tricuspid seal at a lower end.

An insufflation tube 419 with a luer lock 419' extends inside conical upper portion 394 and is attached to membrane 410 so as to provide a fluid communication pathway therethrough.

Figure 52:
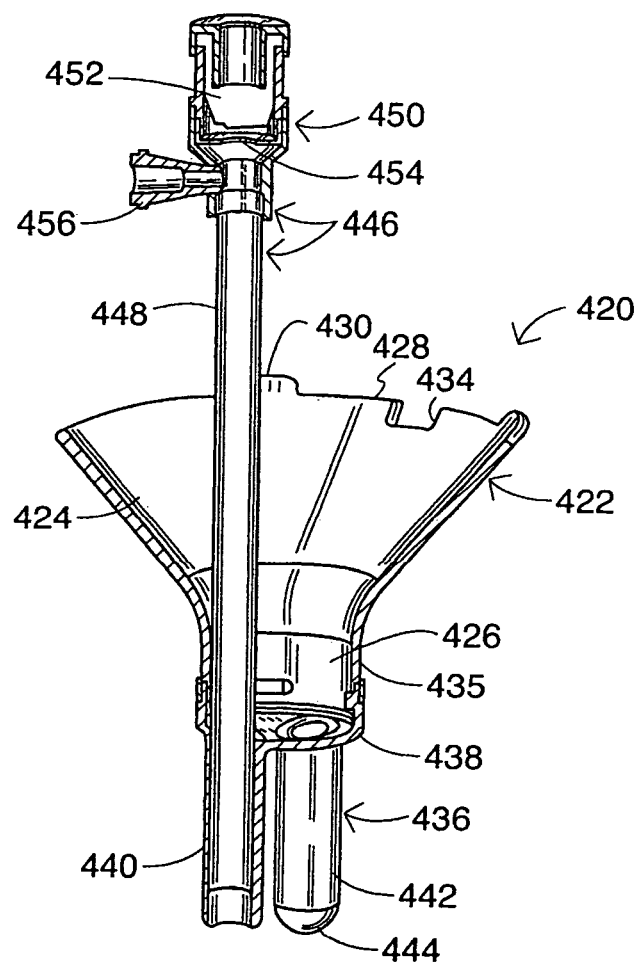
FIG. 52 is a schematic perspective view, partially cut away, of yet a another trocar or port assembly in accordance with the present invention.

As depicted in FIG. 52, a laparoscopic trocar or port assembly 420 comprises a body member 422 including a funnel-shaped upper or proximal portion 424 and a cylindrical lower or distal portion 426. Upper or proximal portion 424 is provided along a circular rim 428 with a plurality of suture anchors 430 in the form of substantially flat, upwardly inclined posts with clamping slots or indentations 432 at rim 428 for receiving tie-down sutures (not shown) to anchor the trocar port assembly 420 to a patient at an incision site (such as the umbilicus). Upper or proximal portion 424 is additionally provided along circular rim 428 with a plurality of rectangular recesses 434 for receiving projections or keys 374 of obturator 370 (see FIGS. 45-47). Cylindrical portion 426 is provided along an outer surface with a helical thread or one or more outwardly extending ribs 435 for enhancing a sealed seating of the cylindrical portion in an incision.

Port assembly 420 further includes, at a bottom or distal end (not separately enumerated) of cylindrical portion 426, an elastomeric "pants" member 436. Pants member 436 includes a base or cannula carrier 438 and tree cannula members in the form of elastomeric legs or downwardly depending fingers 440 and 442 (only two shown). Two legs 442 are each provided with an inwardly extending ring seal (not shown) and a tricuspid seal at a lower or distal end 444. Leg 440 is dedicated to the passage of a scope (not shown) and is provided with a dedicated cannula 446 having a tubular member 448 that is inserted into leg 440 and rests at a lower end against a shoulder 448 on an inner surface (not designated) of leg 440. At an upper or proximal end, cannula 446 has a valve assembly 450 including a tricuspid seal 452, a ring seal 454, and an insufflation port 456. Cannula 446 may be removably inserted into leg 440 and held there by a friction fit.

Legs or fingers 442 may be provided internally with stiffening tubes (not shown) that provide strength and rigidity and reduce friction. Legs 442 are flexible at least in a region of attachment to carrier 438, whereby the legs/fingers/cannulas may be temporarily bent into inclined attitudes in response to forces exerted via laparoscopic instruments shafts during a surgical procedure.

As illustrated in drawings described hereinabove, a skirt for a trocar or surgical port assembly for minimally invasive surgery has a 360° circumferential extent. However, it is possible for a trocar or port assembly skirt to extend less than 360° around. This can be particularly useful where the trocar or port assembly is purposefully or inadvertently dislodged from a fully inserted position. In that event, a partial skirt with a longitudinal gap or slot can contract and close the slot, thereby permitting further instrument movements while still providing protection to abdominal wall tissues.

A partial skirt may provide for a better range of motions than a full skirt. When instruments are at their extreme lateral positions, a full skirt may restrict the instruments' movements, while partial skirt will not. Moreover, in practice the skirt must be attached (glued, etc.) to the rigid portion of the port. A full skirt will occupy the entire circumference of the cylindrical portion of the port assembly body member, while a partial skirt will occupy only a section of the cylindrical portion. The consequential spatial reduction may be significant when a small cavity wall incision is necessary or desirable. Finally, a partial skirt might be less expensive to manufacture.

As disclosed herein, a skirt may be used in combination with seal-containing cannulas or fingers that extend either above or below the body of a surgical port assembly. In the latter case, one or more downwardly depending cannulas or leg members may be used in combination with a full or partial skirt. The cannulas or fingers may be shortened while still carrying the sealing elements, while the skirt serves the tissue protection function.

A cannula module pursuant to the present disclosure may comprise a cannula-carrying member and a plurality of cannulas, fingers, or legs attached thereto. As discussed hereinabove, the carrier member may be dome-shaped above or below the body member of a surgical port assembly. The cannula module may be removably attached to a port assembly body member to enable switching of one cannula module with another during a surgical procedure, depending on specific exigencies as they arise. Thus, an "octopus" module with two legs (for a scope and one larger instrument) could replace a module with three legs or cannulas. When a cannula module is removed, the opening in the body member could be used for tissue evacuation or other procedure that requires a large access opening. Pneumoperitoneum is quickly re-established upon connection of a new cannula module. A temporary port plug fitting into the opening of the body member (e.g., into a cylindrical portion) may be provided to minimize this inconvenience. A plug minimizes or eliminates gas leakage from the abdomen of the patient during an exchange of the instruments.

Figure 53:
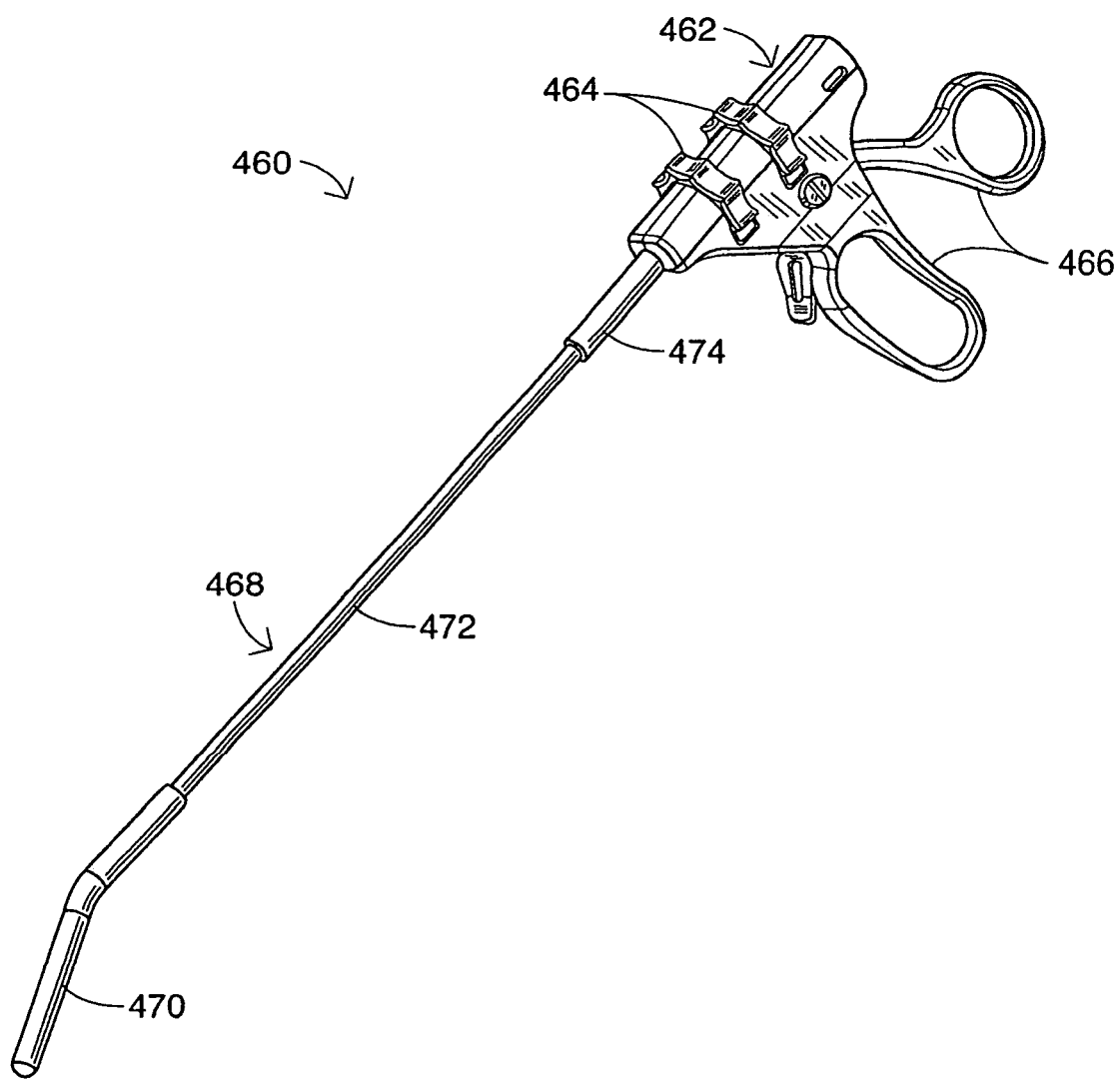
FIG. 53 is a schematic perspective view of a laparoscopic instrument for use with a surgical port assembly in accordance with the present invention.

The present invention can accommodate special hand instruments where the portion of the instrument shaft traversing the port assembly has a smaller diameter than the distal and/or proximal portion. As illustrated in FIG. 53, a laparoscopic instrument 460 includes a handle 462 with actuators or controls 464 and 466 and an elongate shaft 468. Shaft 468 includes an enlarged distal end portion 470 incorporating operative components (not shown), a thin middle section 472 and an enlarged proximal portion 474 connected to handle 462. Such a terminally enlarged instrument 460 can function with a detachable "octopus" with a special "C-shaped" channel. The instrument shaft 468 is sealed between the "C" and the internal wall of the funnel. The smaller diameter cross-section of middle section 472 allows one to maximize the range of motion that is limited by the port's internal diameter. Such an instrument 460 can serve to free up as much space in the restricted area as possible. The longitudinal cross-section of the instrument shaft 468 has an hour-glass (thin waist) configuration. A seal is established by the instrument seal(s)—one or several—which are located inside the cannula and hug the instrument tightly. Since the seals are very flexible, these would not restrict (seals will be deflected) the movements of the larger diameter sections (distal and proximal), but will not allow for gaps between the seals and the central or middle section 472 of the instrument shaft 468.

Figures 54, 55:
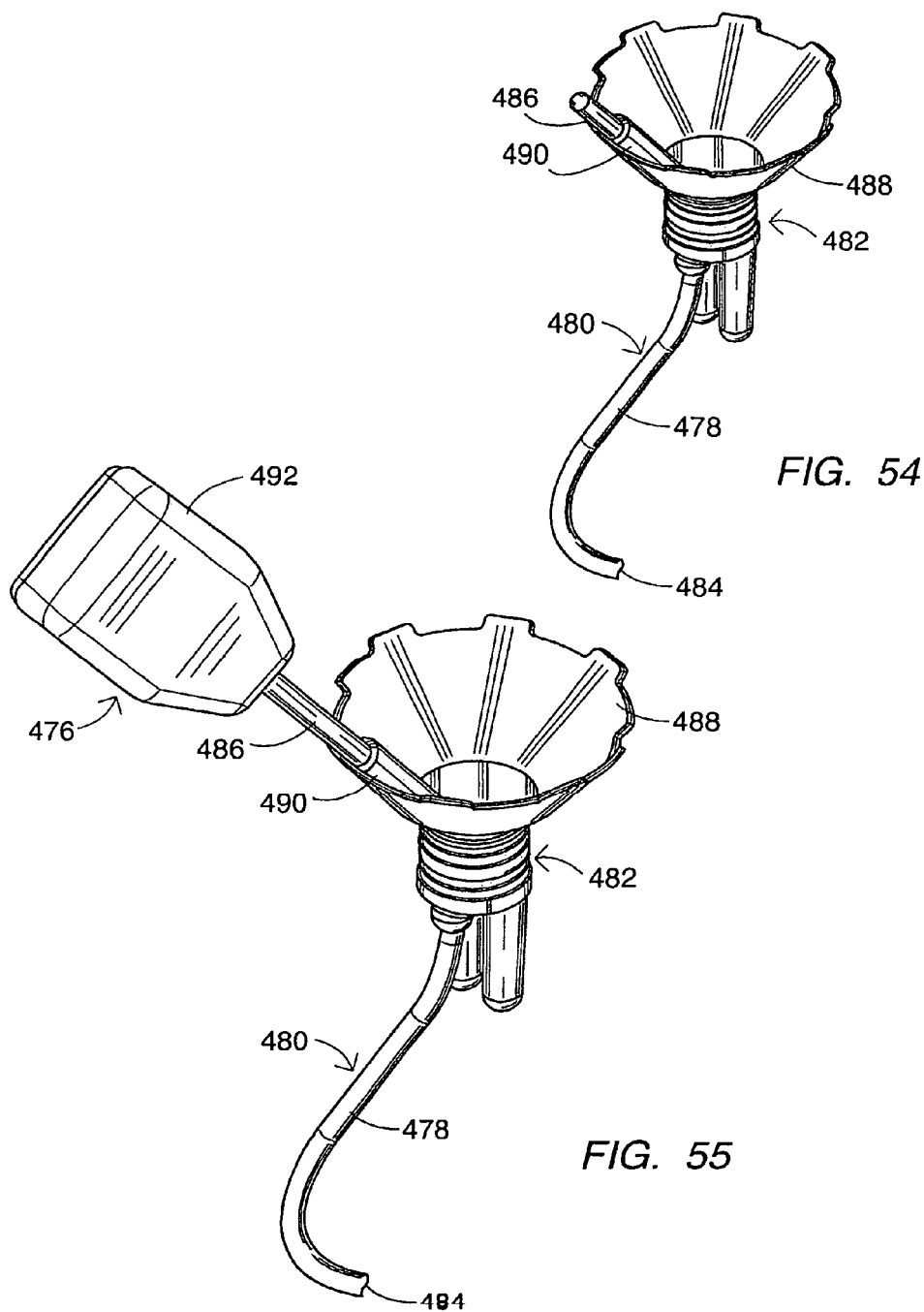
FIG. 54 is a schematic perspective view of a surgical port assembly with an integrated endoscope shaft or arm, in accordance with the present invention.
FIG. 55 is a schematic perspective view, similar to FIG. 54 but on a larger scale, showing a functional housing component on a proximal end of the endoscope shaft or arm of FIG. 54.
Figure 56:
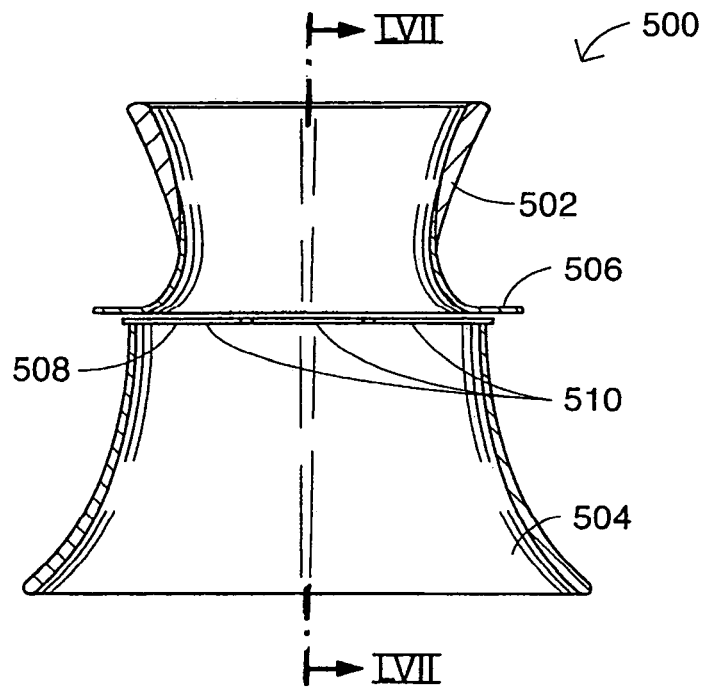
FIG. 56 is a schematic cross-sectional view of a thoracic surgical port in accordance with the present invention, taken along a wide dimension of the port, line LVI-LVI in FIG. 57.
Figure 57:
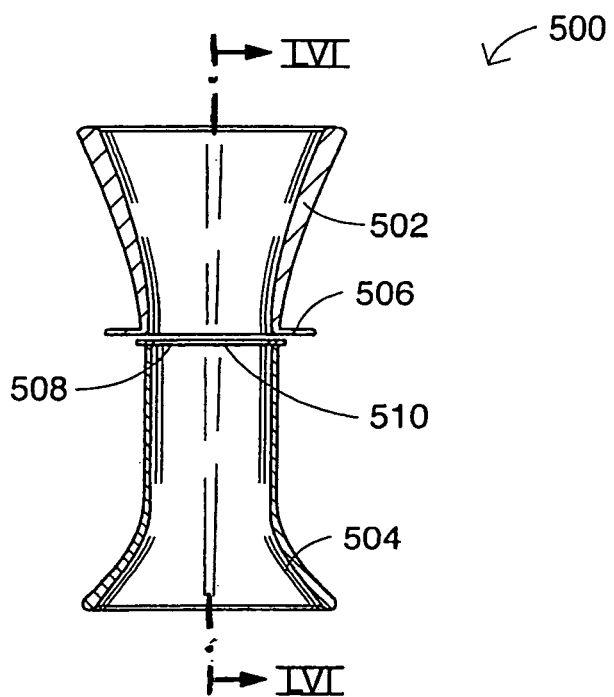
FIG. 57 a schematic cross-sectional view of a thoracic surgical port, taken along a narrow dimension of the port, line LVII-LVII in FIG. 58.
Figure 58:
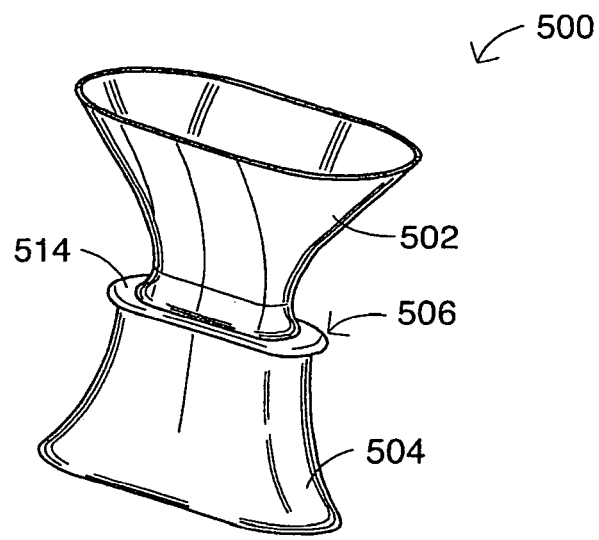
FIG. 58 is a schematic perspective view of the thoracic surgical port of FIGS. 56 and 57.

A surgical port assembly as described herein may be provided with a built-in or integrated endoscope 476, as depicted in FIGS. 54 and 55. A distal portion 478 of a scope arm 480 extending from an underside of a port assembly body member 482 is flexible and incorporates digital chip technology such as a charge-coupled device (not shown) at a distal end 484. In this design, only a small electrical cable need pass through the body member 482 of the surgical port assembly at the patient interface or skin surface, thereby reducing the scope's impact on the "effective" cross-section of the port and improving on the degree of motion. The built-in camera is maneuverable via cables (not shown) in the bendable shaft or arm 480. The cables may extend through the port's body member 482 to the proximal side thereof. Alternatively, orientation control may be effectuated wirelessly. In the latter case, a wireless receiver (not shown) may be integrated into the port body member 482 or the distal end portion 478 of scope arm or shaft 480. Motors (not shown) may be provided in scope arm 480 for bending distal end portion 478 in response to incoming wireless control signals.

As shown in FIGS. 54 and 55, scope arm or shaft 480 has a proximal end portion 486 that extends along a funnel-shaped portion 488 of body member 482 and is permanently or removably connected thereto. Specifically, proximal portion 486 passes through a sleeve 490 attached to funnel-shaped body portion 488. Alternatively, proximal shaft portion 486 may be partially or completely embedded in the wall of funnel-shaped body portion 488. Proximal shaft portion 486 is connected or connectable to an endoscope functional module 492 that may carry bending actuators or control knobs (not illustrated), a light source (not illustrated), electrical cables (not illustrated) for connecting to a video monitor, etc.

An integrated scope as shown in FIGS. 54 and 55 provides the required image using as little space as possible in the space-restricted area, that is, at the patient interface or skin surface. It is to be noted that rigid laparoscopes with all their straight proximal shafts substantial occupy space above the cannula holder or port assembly and thus interfere with the manipulation of "working" instruments. Existing flexible endoscopes do not provide sufficient visualization and are too fragile and too expensive. The design described above with respect to FIGS. 54 and 55 overcome these drawback.

As depicted in FIGS. 56-59, a thoracic surgical port 500 comprises a downwardly tapering, substantially flexible, upper or proximal part 502 and an upwardly tapering, substantially flexible lower or distal part 504. During use, upper part 502 is located subcutaneously, while lower part 504 extends in between the ribs of a patient into a pleural space. A substantially rigid ring-like structure 506 is located, during use of surgical port 500, on top of the patient's ribs (not shown). Ring structure 506 surrounds an interface or junction between upper part 502 and lower part 504. Upper part 502 is smaller than lower part 504. This allows one to make a smaller skin incision. Lower part 504 is larger and is accommodated in a slightly larger muscle-splitting incision (not shown) between ribs. A flexible membrane 508 is located inside the port at the level of ring structure 506. Membrane 508 must be located in the proximity of the ribs—the restriction zone—in order to maximize the range of instrument freedom. Membrane 508 carries a variety of openings 510 for passage of the instruments (not shown). Membrane 508 and multiple openings 510 are needed (instead of one big opening) to provide the instruments with individual pivot points and individual compartments. This configuration improves surgeon ergonomics and minimizes the interference of instruments with each other. Rigid ring structure 506, sitting atop the ribs, provides stability of the port 500. Ring structure 506 does not slide into the chest and provides pivot points for the instruments. Ring structure 506 sits in a soft tissue pocket created by a surgeon with gentle finger dissection just above the patient's ribs. Also, in combination with a smaller skin incision, ring structure 506 eliminates the need for fixing the port 500 to the patient's chest. Port 500 is mobile but stable in the deployed location.

Ring structure 506 is a part of the entire thoracic port unit 500 and does not become detached from the rest of the unit when the unit is inserted in place. Ring structure 506 can be attached to upper part 502 and/or lower part 504 or to neither of those parts (attached instead to horizontal membrane 508), depending on manufacturing needs.

Upper part 502 and lower part 504 can have different durometer values. Upper and lower parts 502 and 504 can have the same flexibility, a similar flexibility, or a substantially different flexibility depending on the needs of the operator and the procedure. Upper and lower parts 502 and 504 can be permanently glued to one another during manufacture or could be manufactured (molded) as a single integral unit. Upper and lower parts 502 and 504 can be slidably attached to each other. For example, (1) lower part 504 may slide into upper part 502, which carries the rigid ring 506, (2) upper part 502 may slide into lower part 504, which carries the rigid ring 506, (3) upper and lower parts 502 and 504 may slide into a horizontal plate (a rigid membrane 508) that has openings 510 for the instruments and is surrounded by the rigid ring 506.

In any event, the rigid ring structure 506 sits on top of the patient's ribs. There is no need to fix the port 500 to the surrounding tissues, either with sutures of some other connectors. The port assembly 500 will stay in place.

Figure 59:
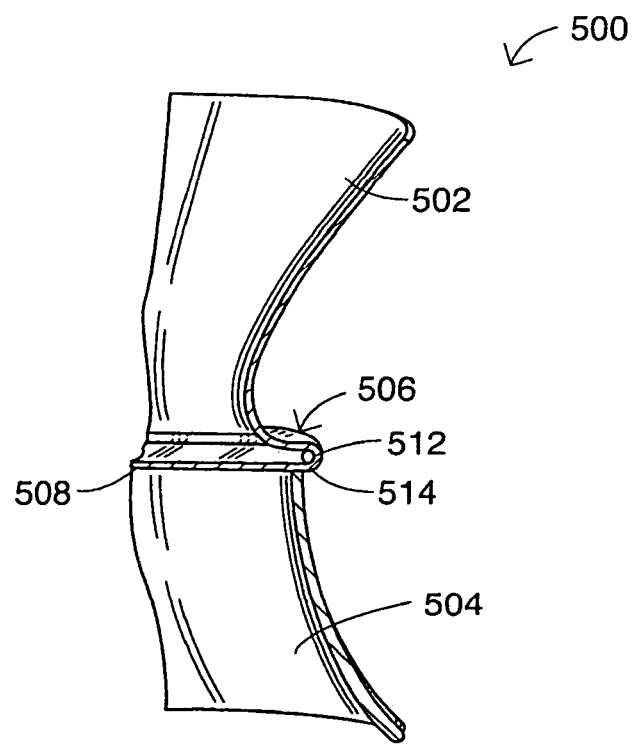
FIG. 59 is a broken-away schematic perspective view, on a larger scale, of the thoracic surgical port of FIGS. 56-58.

As depicted in FIG. 59, a rigid ring 512 seated inside a hollow flange 514 may form ring structure 506. Flange 514 is continuous with upper part 502 and membrane 508.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical port component comprising:
a body including;
   a cylindrical portion formed by a plurality of sections or flaps, said cylindrical portion including at least one proximally extending projection at a proximal end thereof; and
   a ring-shaped base member extending transversely across said cylindrical portion at the proximal end thereof, said ring-shaped base member including at least one slot configured and disposed to receive, at said proximal end of said cylindrical portion, said at least one proximally extending projection at said proximal end of said cylindrical portion, said sections or flaps being swingably coupled, at said proximal end of said cylindrical portion, to said ring-shaped base member when said at least one proximally extending projection of said cylindrical portion is received in said at least one slot of said ring-shaped base member, said at least one proximally extending projection extending proximally through said at least one slot of said ring-shaped base member such that said at least one proximally extending projection extends proximally from said ring-shaped base member when said at least one proximally extending projection of said cylindrical portion is received in said at least one slot of said ring-shaped base member,
said sections or flaps being made of at least a substantially rigid material, said ring-shaped base member including a plurality of upwardly or proximally extending arcuate flange sections receivable into a distal or lower end of a cylindrical body of a flexible-cannula port member.

2. The surgical port component defined in claim 1, further comprising an at least partially flexible skirt including a cylindrical proximal sleeve fitting over said sections or flaps, thereby coupling said skirt to said body.

3. The surgical port component defined in claim 1, wherein said sections or flaps are coupled to said ring-shaped base member after said at least one proximally extending projection of said cylindrical portion is received in said at least one slot of said ring-shaped base member.

* * * * *